(12) United States Patent  
Almirante et al.

(10) Patent No.: US 8,003,811 B2
(45) Date of Patent: Aug. 23, 2011

(54) NITRIC OXIDE DONOR COMPOUNDS

(75) Inventors: Nicoletta Almirante, Milan (IT); Silvia Stefanini, San Donato Milanese (IT); Laura Storoni, Cesano Maderno (IT); Fabio Nicoli, Milan (IT); Julio Lazaro Padron, Ardea (IT); Stefano Biondi, Pero (IT)

(73) Assignee: Nicox S.A., Sophia Antipolis Valbonne (FR)

( * ) Notice: Subject to any disclaimer, the term of this patent is extended or adjusted under 35 U.S.C. 154(b) by 0 days.

(21) Appl. No.: 12/744,168

(22) PCT Filed: Jan. 15, 2009

(86) PCT No.: PCT/EP2009/050416
§ 371 (c)(1),
(2), (4) Date: May 21, 2010

(87) PCT Pub. No.: WO2009/098113
PCT Pub. Date: Aug. 13, 2009

(65) Prior Publication Data
US 2010/0249189 A1    Sep. 30, 2010

Related U.S. Application Data

(60) Provisional application No. 61/006,946, filed on Feb. 7, 2008.

(51) Int. Cl.
*C07D 493/00* (2006.01)
*A61K 31/45* (2006.01)

(52) U.S. Cl. ........................................ 549/464; 514/321

(58) Field of Classification Search .................. 549/464; 546/197; 514/321, 470
See application file for complete search history.

(56) References Cited

FOREIGN PATENT DOCUMENTS

EP    0 361 156 A    4/1990

OTHER PUBLICATIONS

Stoss et al Arzneimittel-Forschung 1990, 40, 13-18.*
Miller M R et al: "Recent developments in nitric oxide donor drugs." British Journal of Pharmacology Jun. 2007, vol. 151, No. 3, Jun. 2007 pp. 305-321, XP00252052 ISSN: 0007-1188.

Megson Ian L et al: "Nitric oxide donor drugs: current status and future trends." Expert Opinion on Investigational Drugs May 2002, vol. 11, No. 5, May 2002, pp. 587-601, XP002520653 ISSN: 1354-3787.

* cited by examiner

*Primary Examiner* — Rita Desai
*Assistant Examiner* — John Mabry
(74) *Attorney, Agent, or Firm* — Arent Fox LLP

(57) ABSTRACT

The invention relates to nitric oxide donors of the formula (I) and pharmaceutically acceptable salts or stereoisomers thereof:

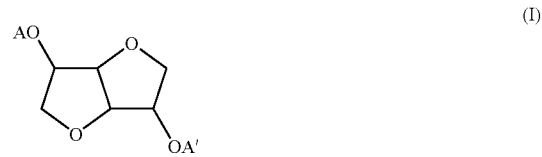

(I)

wherein A and A' are independently selected from the group consisting of H and —(X)$_s$—Y with the proviso that at least one of A or A' is not H;
wherein
s is 0 or 1;
X is selected from the group consisting of:
—CO—, —COO—, —CONH— and —SO$_2$— or

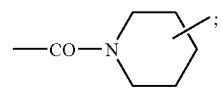

Y is
straight or branched C$_1$-C$_{20}$ alkyl chain, preferably C$_1$-C$_{10}$ alkyl chain, substituted with one or two —ONO$_2$; or
C$_1$-C$_6$ alkylenoxy-C$_1$-C$_5$ alkyl wherein the alkyl group is substituted by one or two —ONO$_2$ groups.
The invention also provides novel compositions comprising at least one compound of the invention and at least one therapeutic agent.

12 Claims, No Drawings

NITRIC OXIDE DONOR COMPOUNDS

CROSS-REFERENCED TO RELATED APPLICATION

This application is a National Stage entry of International Application No. PCT/EP2009/050416, filed Jan. 15, 2009, which claims priority of U.S. Application No. 61/006,946, filed Feb. 7, 2008. The disclosure of the prior application is hereby incorporated in its entirety by reference.

The invention relates to nitric oxide donor compounds and pharmaceutical compositions containing them. The invention also provides novel compositions comprising a compound of the invention and at least one therapeutic agent.

The invention also relates to the use of the nitric oxide donor compounds and their compositions for treating cardiovascular diseases, hypertension, inflammation, pain, fever, gastrointestinal disorders, ophthalmic diseases, glaucoma, ocular hypertension, hepatic disorders, renal diseases, nephropathies, diabetes, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation, vascular diseases, neurodegenerative disorders, metabolic syndrome, Reynolds' syndrome, scleroderma, muscular dystrophies such as Duchenne and Becker dystrophies.

Nitric oxide donor compounds (NO donors) are pharmacologically active substances that, in vivo or in vitro, release NO.

The organic nitrates are the most commonly used NO donors. Glyceryl trinitrate (GTN, also known as nitroglycerin) is the best-studied nitrate, used mainly in acute relief of pain associated with angina, whereas other slower release preparations, such as isosorbide mononitrate (ISMN), are used for the treatment of chronic angina.

The main limitation of the organic nitrates is the well-documented development of tolerance with prolonged continuous use. The only reliable means to avoid tolerance is to incorporate a nitrate-free interval in the therapeutic regimen, which can be problematic for some forms of angina and is a clear impediment to the use of nitrates for management of chronic conditions (British Journal of Pharmacology (2007) 151, 305-321).

The other clinically relevant NO donor in current use is sodium nitroprusside (SNP). SNP is used on-site in hospitals to provide rapid lowering of blood pressure in hypertensive crises. SNP is also the drug of choice in clinical studies, where it is recognized as the gold standard NO-dependent, but endothelium-independent vasodilator. Of particular concern with this NO donor is the potential release of any of the five cyanide groups incorporated in the structure. Indeed, there have been isolated reports that long-term use of this agent can be associated with cases of cyanidosis, albeit rarely.

Further limitations for the use of SNP are its requirement for intravenous administration, sensitivity to photolysis once in solution and its remarkable potency, which can make dose titration difficult.

Other known methods of NO delivery include soluble, short-term NO donors, such as S-nitroso-N-acetyl-D,L-penicillamine (SNAP) and incorporation of NO donors into polymeric matrices. In general, NO-nucleophile complexes (e.g., diazeniumdiolate ions) and NO-donating groups (e.g., S-nitrosothiols) may spontaneously decompose in aqueous environments, such as physiological fluids, to release NO. This rapid, spontaneous decomposition, however, may not be a favourable property for many therapeutic applications. Generally, a slower rate of decomposition and more steady evolution of NO are more efficacious.

Arzneimittelforschung. 1990 January, 40(1):13-18 discloses hybrid molecules which contain both the 1,4:3,6-dianhydro-hexitol (isohexide) and glycerol partial structures, with nitrate ester groups at different positions. Pharmacological screening shows that the new structures are much less active than the parent compounds.

The invention is directed to compounds that are particularly useful as nitric oxide donors having an improved pharmacological profile.

In one embodiment, the invention is directed to a compound of the formula (I) and pharmaceutically acceptable salts or stereoisomers thereof:

(I)

wherein A and A' are independently selected from the group consisting of H and $-(X)_s-Y$ with the proviso that at least one of A or A' is not H;
wherein
s is 0 or 1;
X is selected from the group consisting of:
$-CO-$, $-COO-$, $-CONH-$ and $-SO_2-$ or

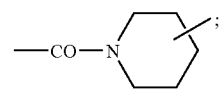

Y is
straight or branched $C_1$-$C_{20}$ alkyl chain, preferably $C_1$-$C_{10}$ alkyl chain, substituted with one or two $-ONO_2$, or $C_1$-$C_6$ alkylenoxy-$C_1$-$C_5$ alkyl wherein the alkyl group is substituted by one or two $-ONO_2$ groups.
In a preferred embodiment Y is selected from the group consisting of:
1) $Z-CH_2-NO_2$,
wherein Z is a straight or branched $C_1$-$C_{10}$ alkylene, preferably a straight or branched $C_1$-$C_6$ alkylene;
2) $(CH_2)_n R^1$,
3) $(CH_2)_n-O-CH_2-R^1$,
wherein
$R^1$ is $-CH(ONO_2)R^2$;
$R^2$ is $-CH_3$ or $C_{1-4}$ alkyl;
n is an integer from 1 to 6;
4) $Y^1-R^3$,
wherein
$R^3$ is $-CH(ONO_2) CH(ONO_2) R^4$;
$R^4$ is selected from $-CH_3$, $-CH_2CH_3$ and $-CH(CH_3)_2$;
$Y^1$ is $-(CH_2)_{1-4}-(X^1)_{0-1}-(CH_2)_{0-4}$, wherein $X^1$ is $-O-$ or $-CR^5R^6-$;
and $R^5$ and $R^6$ are independently selected from the group consisting of hydrogen and $C_1$-$C_4$ alkyl;
5) $Y^1-CH(ONO_2) CH_2 (ONO_2)$
wherein $Y^1$ is as above defined, with the proviso that when s is 0, then $Y^1$ is not $-CH_2-$.

The term "$C_1$-$C_{20}$ alkyl" preferably "$C_1$-$C_{10}$" as used herein refers to branched or straight $C_1$-$C_{20}$ or preferably $C_1$-$C_{10}$ hydrocarbon chain such as methyl, ethyl, n-propyl, isopropyl, n-butyl, isobutyl, sec-butyl, t-butyl, pentyl, neopentyl, iso-amyl, exyl, octyl, and the like.

The term "$C_1$-$C_5$ alkyl" and "$C_1$-$C_4$ alkyl" as used herein refers to branched or straight chain alkyl groups comprising one to four or five carbon atoms, including methyl, ethyl, n-propyl, isopropyl, n-butyl, isobutyl, sec-butyl, t-butyl, pentyl, neopentyl, iso-amyl and the like.

The term "$C_1$-$C_{10}$" alkylene or "$C_1$-$C_6$" as used herein refers to branched or straight $C_1$-$C_{10}$ or $C_1$-$C_6$ hydrocarbon chain such as methylene (—$CH_2$—), ethylene (—$CH_2$—$CH_2$—), propylene (—$CH_2$—$CH_2$—$CH_2$—), isopropylene (—$CH_2$($CH_3$)—$CH_2$—), n-butylene (—$CH_2$—$CH_2$—$CH_2$—$CH_2$—), pentylene(—$CH_2$—$CH_2$—$CH_2$—$CH_2$—$CH_2$—) and its branched isomers, n-hexylene (—$CH_2$—$CH_2$—$CH_2$—$CH_2$—$CH_2$—$CH_2$—) and its branched isomers, and the like.

The term "substituted with one or two —$ONO_2$" means that one or two hydrogen atoms of the alkyl chain are substituted with one or two nitroxy group.

The term "$C_1$-$C_6$-alkylenoxy" as used herein refers to "$C_1$-$C_6$-alkylene-O—" wherein the alkylene chain is a branched or straight $C_1$-$C_{10}$ or $C_1$-$C_6$ hydrocarbon chain. Examples of "$C_1$-$C_6$-alkylenoxy" are methylenoxy (—$CH_2O$—), ethylenoxy(—$CH_2$—$CH_2$—O—), propylenoxy (—$CH_2$—$CH_2$—$CH_2$—O—), isopropylenoxy (—$CH_2(CH_3)$—$CH_2$—O), n-butylenoxy (—$CH_2$—$CH_2$—$CH_2$—$CH_2$—O—), pentylenoxy(—$CH_2$—$CH_2$—$CH_2$—$CH_2$—$CH_2$—O—) and its branched isomers, n-hexylenoxy (—$CH_2$—$CH_2$—$CH_2$—$CH_2$—$CH_2$—$CH_2$—O—) and its branched isomers, and the like.

In another embodiment, the compound of formula (I) is selected from the group consisting of:

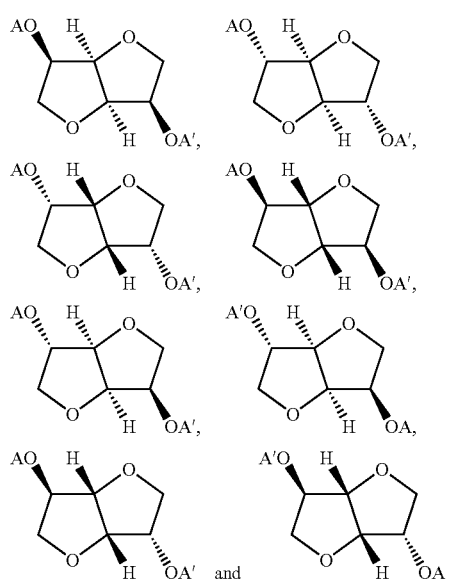

and all other variables are as previously defined.

In another embodiment, the compound of formula (I) is selected from the group consisting of:

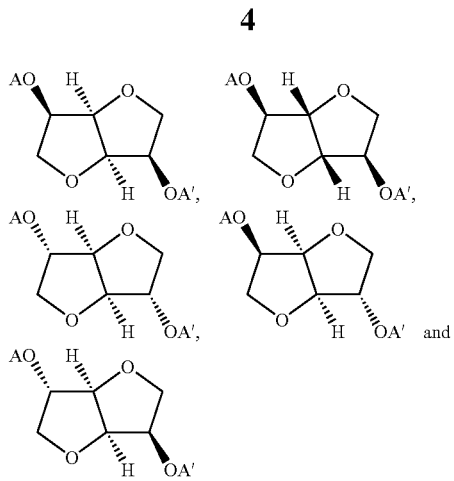

and all other variables are as previously defined.

In another embodiment, the compound of formula (I) is selected from the group consisting of:

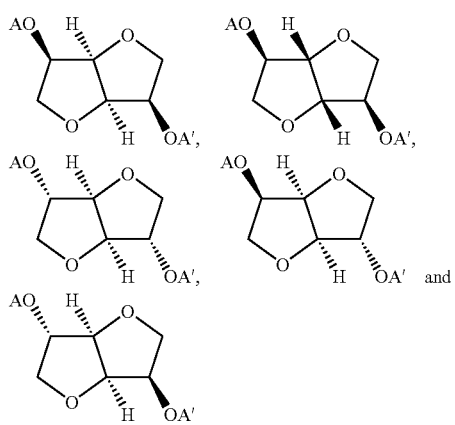

wherein A is H and all other variables are as previously defined.

In another embodiment, the compound of formula (I) is selected from the group consisting of:

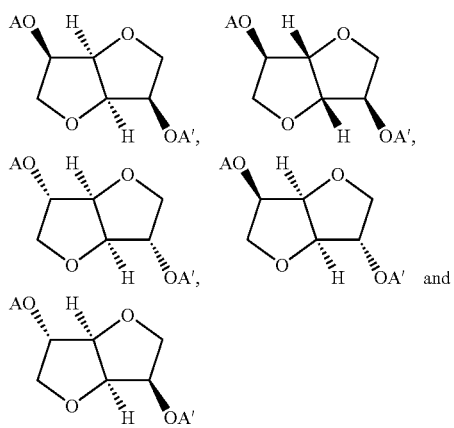

wherein A is H and A' is —CO—Y or —COO—Y.

In another embodiment, the compound of formula (I) is selected from the group consisting of:

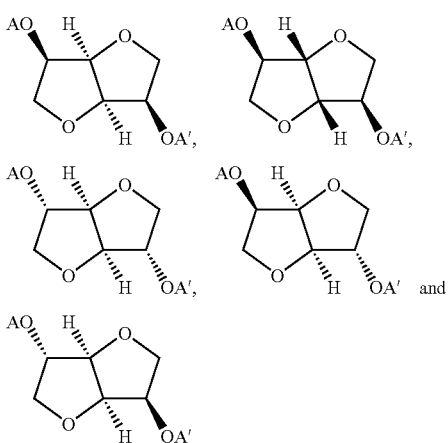
wherein A is H and A' —(X)$_s$—Y wherein s is 0.
In another embodiment, the compound of formula (I) is selected from the group consisting of:
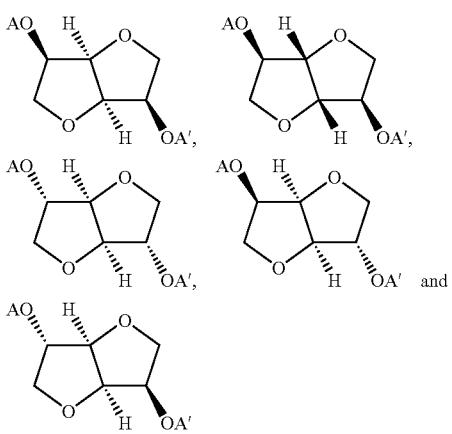
wherein A is H and A' is
In another embodiment, Y is selected from the group consisting of:
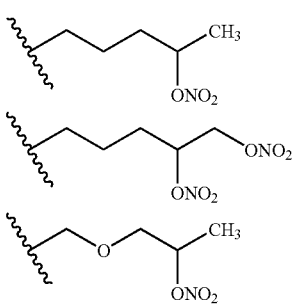
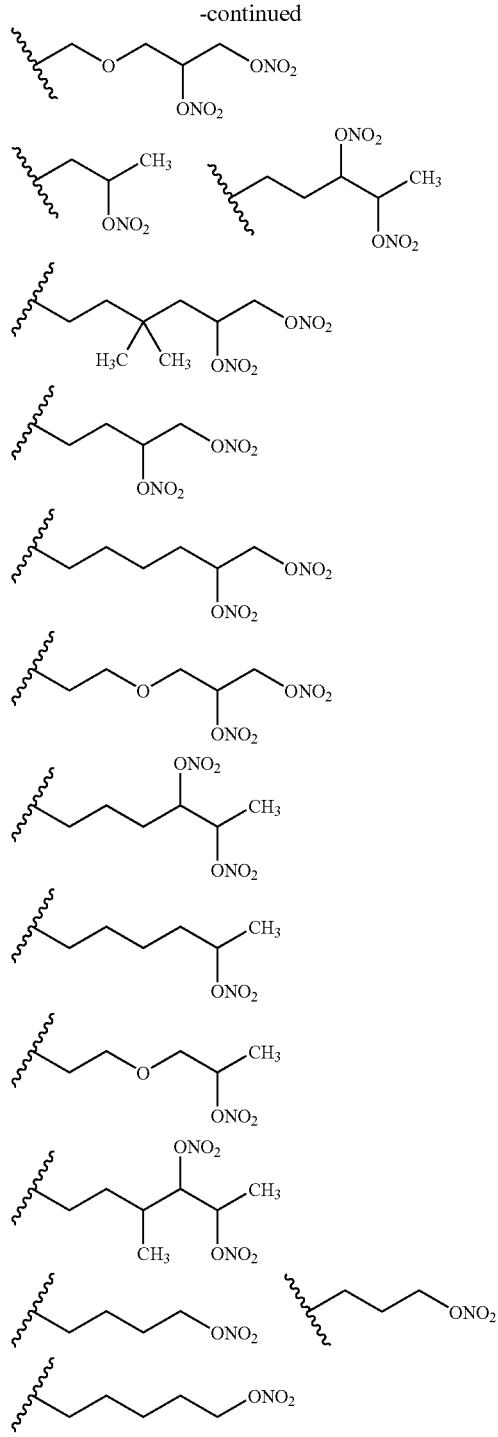
The following are preferred compounds according to the present invention:
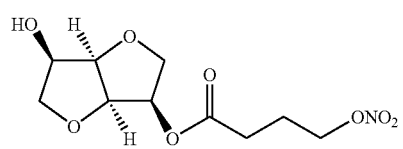
(1)

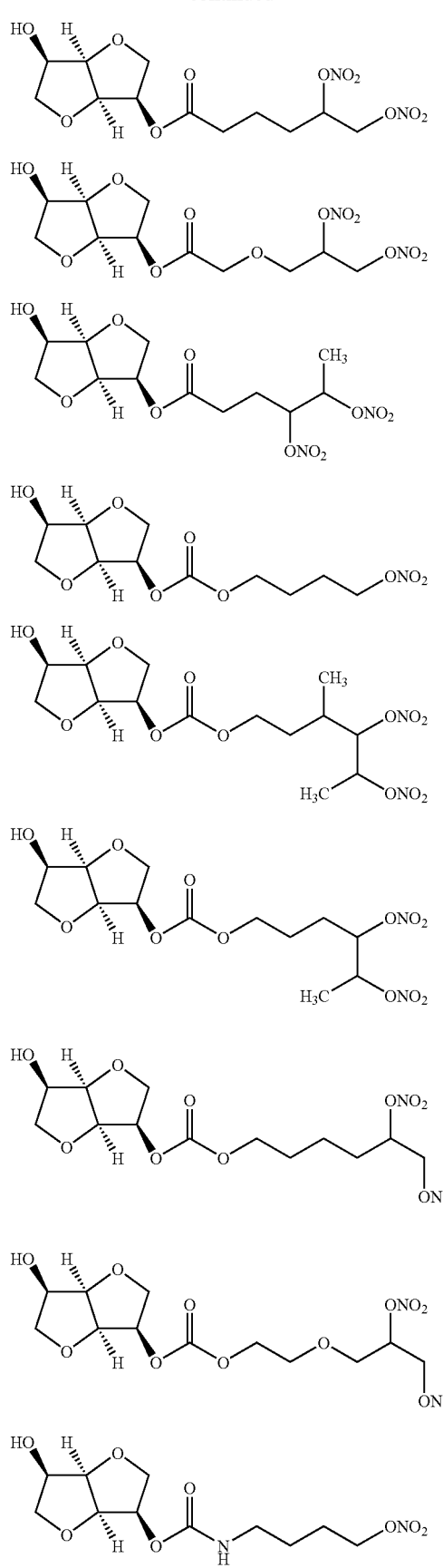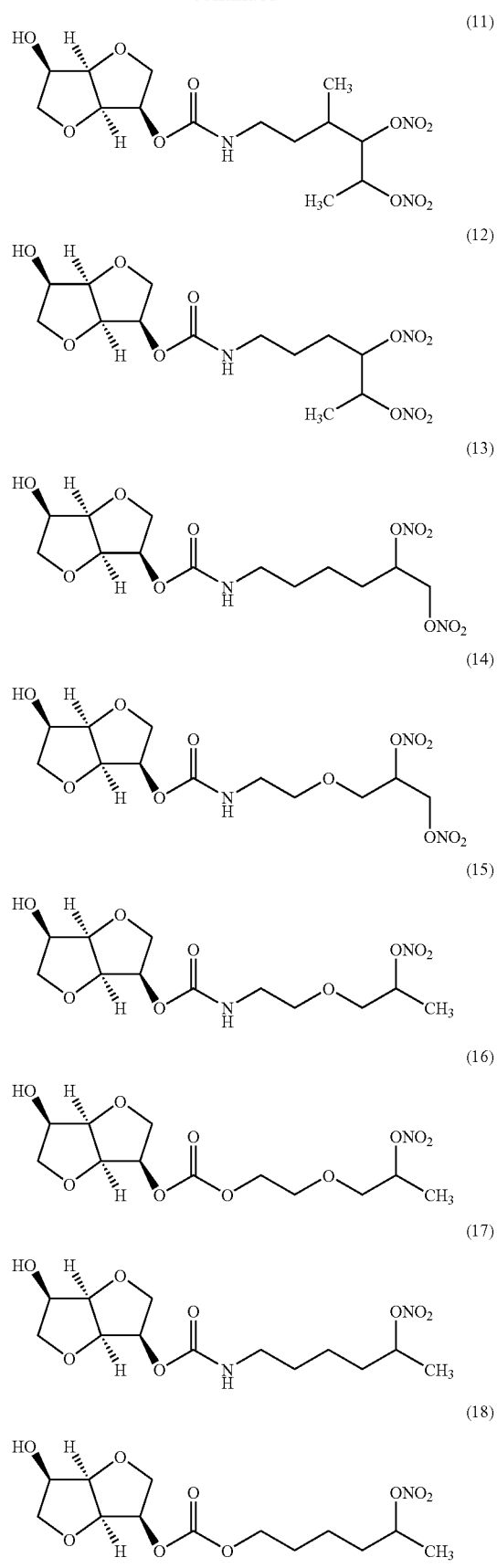

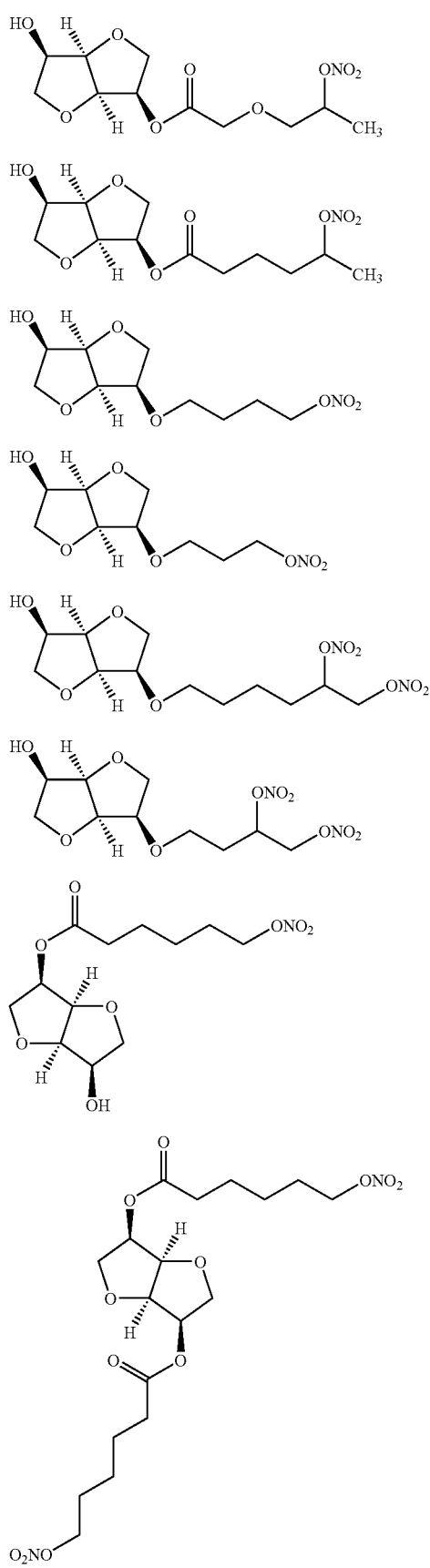
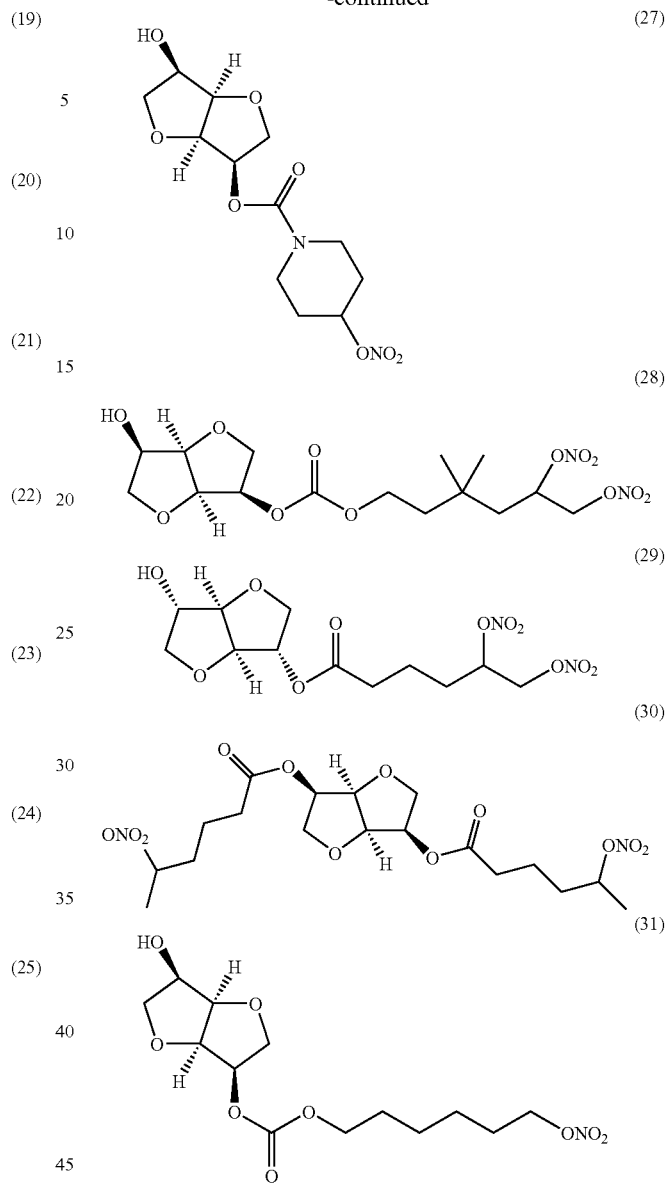

or steroisomers thereof.

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

The invention also relates to the use of the compounds of formula (I) or their salts for treating cardiovascular diseases, hypertension, inflammation, pain, fever, gastrointestinal disorders, ophthalmic diseases, glaucoma, ocular hypertension, hepatic disorders, renal diseases, nephropathies, diabetes, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation, vascular diseases, neurodegenerative disorders, metabolic syndrome, Reynolds' syndrome, scleroderma, muscular dystrophies such as Duchenne and Becker dystrophies.

The compounds of formula (I) or their salts can be used in combination with at least one therapeutic agent such as non steroidal anti-inflammatory drugs, anti-thrombotic drugs, steroidal anti-inflammatory drugs, ACE inhibitors, Angiotensin II receptor antagonist, β-adrenergic receptor blockers, β-adrenergic receptor agonists, statins, prostaglandins for the treatment of cardiovascular diseases, hypertension, inflammation, pain, fever, gastrointestinal disorders, ophthalmic diseases, glaucoma, ocular hypertension, hepatic disorders, renal diseases, nephropathies, diabetes, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation such as cancer, vascular diseases, neurodegenerative disorders, metabolic syndrome, Reynolds' syndrome, scleroderma, muscular dystrophies such as Duchenne and Becker dystrophies.
The expression "in combination" means that the compounds can be administered separately or in form of a composition.

Another embodiment of the present invention relates to compositions comprising the compounds of formula (I) or their salt at least one therapeutic agent selected from: non steroidal anti-inflammatory drugs, anti-thrombotic drugs, steroidal anti-inflammatory drugs, ACE inhibitors, Angiotensin II receptor antagonist, β-adrenergic receptor blockers, β-adrenergic receptor agonists, statins, prostaglandins.

The invention also provides kits comprising at least a compound of formula (I) or its salts and at least one therapeutic agent selected from: non steroidal anti-inflammatory drugs, anti-thrombotic drugs, steroidal anti-inflammatory drugs, ACE inhibitors, Angiotensin II receptor antagonist, β-adrenergic receptor blockers, β-adrenergic receptor agonists, statins, prostaglandins.

An object of the present invention is also pharmaceutical compositions containing at least a compound of the present invention of formula (I) together with non toxic adiuvants and/or carriers usually employed in the pharmaceutical field.

The daily dose of active ingredient that should be administered can be a single dose or it can be an effective amount divided into several smaller doses that are to be administered throughout the day. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or iontophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavouring and the like.

The compounds of the present invention show significant advantages over the precursor compounds.

General Synthesis

1. The compounds of general formula (I) as above defined

(I)

wherein A is H or is equal to A' where A' is —(X)$_s$—Y wherein s is 0 and Y is as above defined can be obtained: by reacting compounds (IIa) or (IIb)

(IIa)

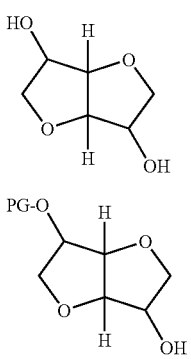

(IIb)

wherein PG is a protective group such as allyl, trialkylsilyl, tetrahydropiranyl with one equivalent or more than one equivalent of a compound of formula (IIIa):

Hal—Y (IIIa)

wherein Y is as above defined, in the presence of an organic or inorganic base such as NaH, DBU, in an aprotic polar solvent such as THF, DMF at temperatures ranging between −20° C. to 100° C., eventually removing the protective group, when present, with methods known in the literature.

Compounds (IIb) can be prepared by compounds (IIa) by known methods (see for example: T. W. Greene, P. G. M. Wuts "Protective groups in organic Synthesis", 4$^{th}$ edition, J. Wiley & Sons, New York, 2006).

Compounds (IIa) are known in the literature or are commercially available, or can be prepared from known compounds by known methods.

Alternatively compound (IIa) or (IIb) can be reacted with a compound of formula (IIIb):

Hal—Y' (IIIb)

wherein Y' contains precursors of the group —ONO$_2$ such as double bond, and/or the group —OH or its precursor as for example a carbonyl group, affording compounds (IIc):

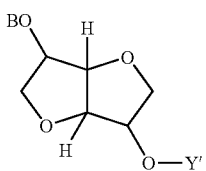

(IIc)

wherein B is PG, H or Y' wherein PG and Y' are as above defined. Compound (IIc) can be converted into compound (I) by nitrating procedure well known in the art, eventually removing the protective group.

Compounds (IIIa) or compounds (IIIb) are known in the literature or can be prepared by known compounds by known procedures.

2. The compounds of general formula (I) as above defined wherein A is H or is equal to A' and A' is —(X)$_s$—Y wherein s is 1 and Y is as above defined can be obtained:

X=—CO— 2a by reacting compounds (IIa) or (IIb) with one or more equivalent of a compound of formula (IIIc)

WOC—Y (IIIc)

wherein W is —OH or a carboxylic activating group such as $C_6F_5$—O— and 4-$NO_2$—$C_6H_4$—O— or is Hal wherein Hal is an halogen atom such as —Cl, —F;

in the presence of a condensing agent such as DCC or CDI, or EDC, or other well known in the art, or in the presence of an organic or inorganic base such as TEA, DIPEA, DBU, in an aprotic polar/apolar solvent such as THF, DMF $CH_2Cl_2$ at temperatures ranging between −20° C. to 100° C., following esterification methods well known in the literature depending on the meaning of W. Eventually removing the protective group, when present, with methods known in the literature.

Alternatively by reacting compounds (IIa) or (IIb) with a compound of formula (IIId):

WOC—Y' (IIId)

wherein W and Y' are as above defined following procedure above defined depending on the meaning of W to afford compound (IId)

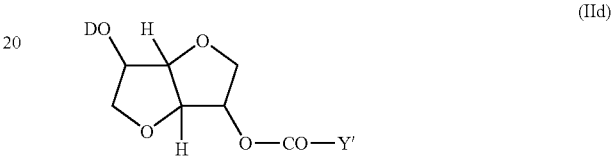

(IId)

wherein D is equal to H, PG or —CO—Y'. Compound (IId) can be converted into compound (I) by nitrating procedure well known in the art, eventually removing the protective group. Compounds (IIIc) and (IIId) are known in the art or can be prepared by known compound following known procedure.

X is —COO— 2b by reacting compounds (IVa):

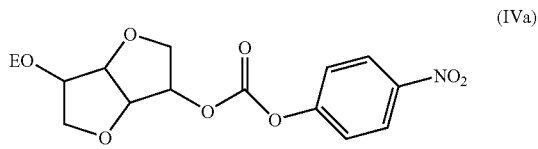

(IVa)

wherein E is H, PG or —$COOC_6H_4$—$NO_2$-p, with one or more equivalent of compounds (IIIe) or compound (IIIf)) wherein Y and Y' are as above defined, HO—Y (IIIe)

HO—Y' (IIIf)

in the presence of an organic or inorganic base such as DMAP, TEA, DIPEA, with or without catalyst such as Sc(OTf)$_3$ in an aprotic polar/apolar solvent such as THF, DMF $CH_2Cl_2$ at temperatures ranging between −20° C. to 100° C., following methods well known in the literature. Optionally nitrating the precursor if Y' is present and eventually removing the protective group, with methods known in the literature. Compound (IVa) can be prepared by reacting compound (IIa) or (IIb) with one or more equivalents of 4-$NO_2$—$C_6H_4$—OCOCl in the presence of an organic or inorganic base such as DMAP, TEA, DIPEA following procedures well known in the literature. Compounds (IIIe) and (IIIf) are known in the literature or can easily be prepared by known compounds and known procedure.

X is —CONH— 2c by reacting compounds (IVa) above defined with compounds (IIIg) Y—NH$_2$ or (IIIh) Y'—NH$_2$ in the presence of an organic or inorganic base such as DMAP, TEA, DIPEA, with or without catalyst such as Sc(OTf)$_3$ in an aprotic polar/apolar solvent such as THF, DMF $CH_2Cl_2$ at temperatures ranging between −20° C. to 100° C., following methods well known in the literature. Optionally nitrating the precursor if Y' is present and removing the protective group, with methods known in the literature. Compounds (IIIg) and (IIIh) are known in the literature or can easily be prepared by known compounds and known procedure.

X is —SO₂—  (2d)

by reacting compounds (IVb)

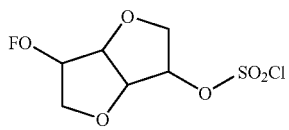
(IVb)

Wherein F is PG or —SO₂Cl with one or more equivalent of compounds (IIIe) or (IIIf) already defined in the presence of an organic or inorganic base such as DMAP, TEA, DIPEA, in an aprotic polar/apolar solvent such as THF, DMF CH₂Cl₂ at temperatures ranging between −20° C. to 100° C., following methods well known in the literature. Optionally nitrating the precursor if Y' is present and removing the protective group, with methods known in the literature.

Compound (IVb) can be prepared by reacting compound (IIa) or (IIb) with one or more equivalents of SO₂Cl₂ in the presence of an organic or inorganic base such as DMAP, TEA, DIPEA following procedures well known in the literature.

The following examples are to further illustrate the invention without limiting it.

Intermediates I and II

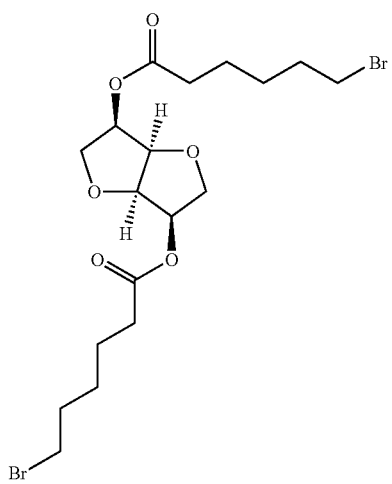

I

II

To a stirred solution of 1,4:3,6-dianhydro-D-mannitol (isommanide) (0.75 g, 5.13 mmol), 6-Br-hexanoic acid (1 g, 5.13 mmol) and DMAP (cat amount) in DCM (50 mL) cooled at 0° C., EDAC (1.47 g, 7.7 mmol) was added. The solution was stirred at room temperature overnight. The solution was washed with a solution of NaHPO₄ 5% (2×40 mL) and brine. The organic layer was dried over sodium sulfate and concentrated under vacuo. The residue was purified by flash chromatography (Biotage SP1, 40+M column, n-Hexane/EtOAc −8:2-4:6) yielding 0.19 g of 1 and 0.5 g of II.

Intermediate I:
¹H NMR (300 MHz, CDCl₃): δ 5.21-5.02 (2H, m), 4.78-4.63 (2H, m), 4.03 (2H, m), 3.79 (2H, m), 3.49 (4H, t), 2.51-2.30 (4H, m), 1.99-1.80 (4H, m), 1.75-1.59 (4H, m), 1.59-1.39 (4H, m).

Intermediate II:
¹H NMR (300 MHz, CDCl₃): δ 5.21-5.03 (1H, m), 4.67 (1H, m), 4.45 (1H, t), 4.35-4.21 (1H, m), 4.15-4.03 (1H, m), 4.01-3.89 (1H, m), 3.88-3.76 (1H, m), 3.63-3.47 (1H, m), 3.38 (2H, t), 2.38 (2H, t), 1.93-1.76 (2H, m), 1.74-1.57 (2H, m), 1.55-1.38 (2H, m).

EXAMPLE 1

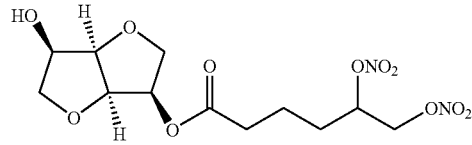

(3R,3aR,6R,6aR)-6-hydroxyhexahydrofuro[3,2-b]furan-3-yl 5,6-bis(nitrooxy)hexanoate (corresponding to compound (2))

Step A: (3R,3aR,6R,6aR)-6-hydroxyhexahydrofuro[3,2-b]furan-3-yl hex-5-enoate

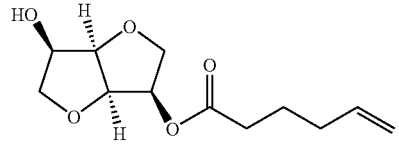

To a stirred solution of 1,4:3,6-dianhydro-D-mannitol (isommanide) (2.00 g, 13.68 mmol), 5-hexenoic acid (1.60 g, 13.68 mmol) and DMAP (0.17 g, 1.4 mmol) in DCM (50 mL) cooled at 0° C., EDAC (3.1 g, 16.42 mmol) was added. The solution was stirred at room temperature for 6 hrs. The solution was diluted with DCM (30 mL), washed with a solution of NaHPO₄ 5% (2×40 mL) and brine. The organic layer was dried over sodium sulfate and concentrated under vacuo. The residue was purified by flash chromatography (Biotage SP1, 40+M column, TLC method: n-Hexane/EtOAc −8:2, Rf product: 0.35) yielding the title compound.

Step B: (3R,3aR,6R,6aR)-6-hydroxyhexahydrofuro[3,2-b]furan-3-yl 5,6-bis(nitrooxy)hexanoate

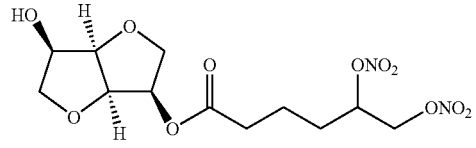

To a stirred solution of (3R,3aR,6R,6aR)-6-hydroxyhexahydrofuro[3,2-b]furan-3-yl hex-5-enoate (1.00 g, 4.13 mmol) and AgNO₃ (0.84 g, 4.95 mmol) in CH₃CN (20 mL)

cooled at −20° C., I₂ (1.26 g, 4.95 mmol) was added. At the end of the addition the mixture was allowed to reach room temperature. AgNO₃ (1.75 g, 10.35 mmol) was added and the mixture was heated in a microwave apparatus (120° C., 40 min). The mixture was filtered through Celite. The filtrate was concentrated under vacuo, diluted with EtOAc, filtered through Celite and concentrated again under vacuo. The residue was purified by flash chromatography (Biotage SP1, SNAP 100 g column, method calculated from TLC: n-hexane/EtOAc 1:1, Rf product: 0.17) affording the title compound.

¹H NMR (300 MHz, CDCl₃): δ 5.40-5.23 (1H, m), 5.23-5.09 (1H, m), 4.83-4.66 (2H, m), 4.59-4.42 (2H, m), 4.39-4.23 (1H, m), 4.17-4.04 (1H, m), 4.03-3.81 (2H, m), 3.67-3.48 (1H, m), 2.65-2.53 (1H, m), 2.53-2.35 (2H, m), 1.92-1.67 (4H, m).

EXAMPLE 2

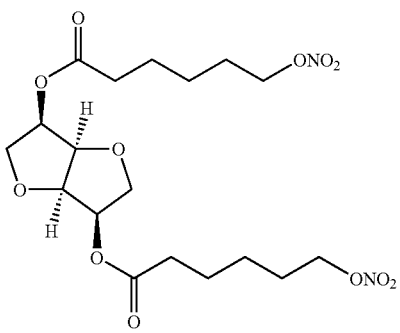

(3R,3aR,6R,6aR)-hexahydrofuro[3,2-b]furan-3,6-diyl bis(6-(nitrooxy)hexanoate) (corresponding to compound (26))

To a stirred solution of Intermediate I (0.19 g, 0.38 mmol) in CH₃CN (10 mL) AgNO₃ (0.193 g, 1.14 mmol) was added and stirred at room temperature. At the end of the reaction the mixture was filtered through Celite. The filtrate was concentrated under vacuo, diluted with EtOAc, filtered through Celite and concentrated again under vacuo. The residue was purified by flash chromatography (Biotage SP1, 12+M column, n-Hexane/EtOAc −8:2) affording the title compound.

¹H NMR (300 MHz, CDCl₃): δ 5.13-5.07 (2H, m), 4.72-4.69 (2H, m), 4.48-4.43 (4H, t), 4.13-4.00 (2H, m), 3.82-3.77 (2H, m), 2.44-2.36 (4H, m), 1.78-1.65 (8H, m), 1.51-1.42 (4H, m).

EXAMPLE 3

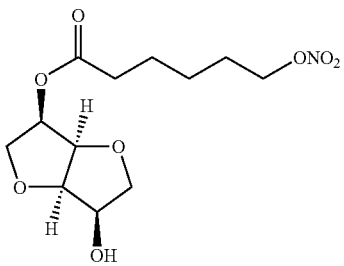

(3R,3aR,6R,6aR)-6-hydroxyhexahydrofuro[3,2-b]furan-3-yl 6-(nitrooxy)hexanoate (corresponding to compound (25))

To a stirred solution of intermediate II (0.5 g, 1.54 mmol) in CH₃CN (10 mL) AgNO₃ (0.34 g, 2 mmol) was added and the reaction was stirred at room temperature. At the end of the reaction the mixture was filtered through Celite. The filtrate was concentrated under vacuo, diluted with EtOAc, filtered through Celite and concentrated again under vacuo. The residue was purified by flash chromatography (Biotage SP1, 25+M column, n-Hexane/EtOAc 6:4-4:6) affording the title compound.

¹H NMR (300 MHz, CDCl₃): δ 5.20-5.14 (1H, m), 4.72-4.69 (1H, m), 4.51-4.44 (3H, m), 4.35-4.26 (1H, m), 4.15-4.09 (1H, m), 4.00-3.95 (1H, m), 3.89-3.83 (1H, m), 3.61-3.55 (1H, m), 2.64-2.61 (1H, d), 2.44-2.34 (2H, m), 1.81-1.66 (4H, m), 1.51-1.42 (2H, m).

EXAMPLE 4

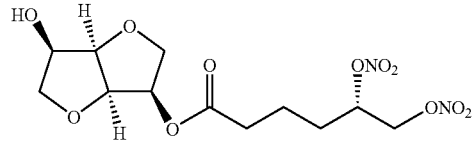

(S)-(3R,3aR,6R,6aR)-6-hydroxyhexahydrofuro[3,2-b]furan-3-yl) 5,6-bis(nitrooxy)hexanoate (corresponding to compound (2) (5S) isomer)

Step A: tert-butyl hex-5-enoate

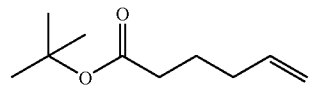

To a solution of 5-hexenoic acid (15.2 mL, 0.131 mol) in DCM (375 mL), cooled to 0° C., tert-butanol (176 mL, 1.84 mol) and then 4-dimethylaminopyridine (3.21 g, 26.3 mmol) were added. The mixture was stirred at room temperature for 22 hrs, filtered and concentrated. The residue was redissolved in DCM/n-hexane and concentrated under reduced pressure. The crude oil was purified by flash chromatography (Biotage SP1, EtOAc/n-hexane from 5 to 10%), affording the title product.

Step B: (S)-tert-butyl 5,6-dihydroxyhexanoate

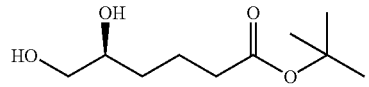

To a suspension of AD-mix alpha (70 g) in water/butanol 1:1 (512 mL) cooled to 0° C., tert-butyl hex-5-enoate (8.5 g, 49.92 mmol) was added. The reaction mixture was stirred at 4° C. for 70 hrs. Then the reaction mixture was cooled to 0° C. and EtOAc (280 mL), followed by continuous portionwise addition of sodium metabisulfite (20.6 g). The mixture was stirred for 30 min at 0° C. and at rt for 1 hour. The organic layer was separated and the aqueous phase extracted with ethyl acetate. The combined organic layers were dried over sodium sulfate and concentrated under reduced pressure. Chromatography over silica gel eluting with EtOAc 100% afforded the title compound as a pale yellow oil.

Step C: (S)-tert-butyl 5,6-di(nitrooxy)hexanoate

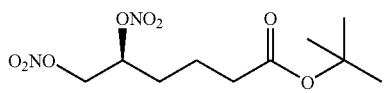

To a solution of fuming nitric acid (10.25 mL, 247.22 mmol) and acetic anhydride (37.6 mL) cooled to 0° C., a solution of (S)-tert-butyl 5,6-dihydroxyhexanoate (10.1 g, 49.44 mmol) in DCM (10 mL) was added dropwise. The reaction mixture was stirred at 0° C. for 1 hour, adjusted to pH 7 by addition of aqueous NaOH and extracted with DCM. The organic layer was separated and the aqueous phase extracted with ethyl acetate. The combined organic layers were dried over sodium sulfate and concentrated under reduced pressure. The crude residue was purified by flash chromatography (Biotage SP1, EtOAc/n-hexane from 10 to 50%), affording the title product as a pale yellow oil.

Step D: (S)-5,6-di(nitrooxy)hexanoic acid

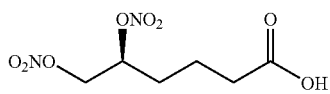

To a solution of (S)-tert-butyl 5,6-di(nitrooxy)hexanoate (12.41 g, 42.155 mmol) in DCM (47 mL) cooled to 0° C. under $N_2$, boron trifluoride diethyl ether complex (5.82 mL, 46.37 mmol) was added. The reaction mixture was stirred at 0° C. for 10 minutes and at rt for 3 hrs. The solution was washed with brine, the organic layer was separated, dried over sodium sulfate and concentrated under reduced pressure. The crude brown oil was used in the next step without further purification.

Step E: (3R,3aR,6R,6aR)-6-(tetrahydro-2H-pyran-2-yloxy)hexahydrofuro[3,2-b]furan-3-ol

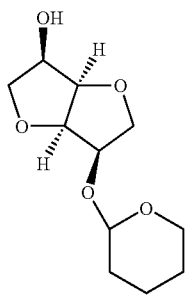

To a solution of 1,4:3,6-dianhydro-D-mannitol (5.00 g, 34.2 mmol) in DCM (102 mL) 3,4-dihydro-2H-pyran (3.88 mL, 42.8 mmol) was added, followed by p-toluensulfonic acid (65 mg, 1.34 mmol). The reaction mixture was stirred at rt for 16 hrs. The solution was washed with brine, the organic layer was separated, dried over sodium sulfate and concentrated under reduced pressure. The crude residue was purified by flash chromatography (Biotage SP1, EtOAc/n-hexane from 30 to 100%), affording the title product as pale yellow oil.

Step F: (5S)-((3R,3aR,6R,6aR)-6-(tetrahydro-2H-pyran-2-yloxy)hexahydrofuro[3,2-b]furan-3-yl) 5,6-bis(nitrooxy)hexanoate To a solution of (3R,3aR,6R,6aR)-6-(tetrahydro-2H-pyran-2-yloxy)hexahydrofuro[3,2-b]furan-3-ol (2.96 g, 12.9 mmol) in DCM (40.8 mL) a solution of the crude (S)-5,6-di(nitrooxy)hexanoic acid (3.06 g, 12.85 mmol) (Step D) in DCM (9.15 mL) was added followed by EDAC (3.69 g, 19.28 mmol) and 4-dimethylaminopyridine (175 mg, 1.28 mmol). The reaction mixture was stirred at rt for 16.5 hrs. The solvent was removed under reduced pressure. The crude residue was purified by flash chromatography (Biotage SP1, EtOAc/n-hexane from 10 to 60%), affording the title product as pale yellow oil.

Step G: (S)-((3R,3aR,6R,6aR)-6-hydroxyhexahydrofuro[3,2-b]furan-3-yl) 5,6-bis(nitrooxy)hexanoate

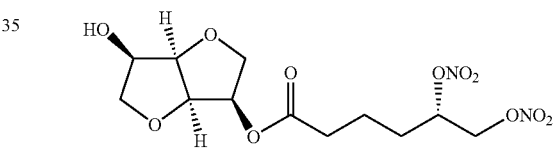

To a solution of (5S)-((3R,3aR,6R,6aR)-6-(tetrahydro-2H-pyran-2-yloxy)hexahydrofuro[3,2-b]furan-3-yl) 5,6-bis(nitrooxy)hexanoate (2.27 g, 5.04 mmol) in ethanol (40 mL) pyridinium p-toluensulfonate (127 mg, 0.504 mmol) was added The reaction mixture was stirred at 45° C. for 4 hrs. The reaction mixture was filtered, concentrated under reduced pressure. The crude residue was purified by flash chromatography (Biotage SP1, EtOAc/n-hexane from 10 to 60%), affording the title product as pale yellow oil.

$^1$H-NMR ((300 MHz, CDCl$_3$): δ 5.30 (1H, dd, 5.16 (1H, q), 4.77 (1H, d), 4.71 (1H, t), 4.50 (2H, m), 4.26 (1H, m), 4.12 (1H, dd), 3.94 (1H, dd), 3.85 (1H, dd), 3.58 (1H, dd), 2.61 (1H, d), 2.47 (2H, m), 1.83 (4H, m).

EXAMPLE 5

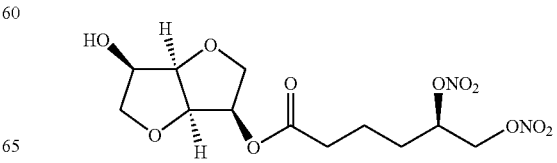

(R)-((3R,3aR,6R,6aR)-6-hydroxyhexahydrofuro[3,2-b]furan-3-yl) 5,6-bis(nitrooxy)hexanoate (corresponding to compound (2) (5R) isomer)

The title compound was prepared by following the procedure for the synthesis of EXAMPLE 4, except that in Step C the reagent ADmix-alpha was replaced by ADmix-beta.

¹H-NMR (300 MHz, CDCl₃): δ 5.38-5.26 (1H, m), 5.18 (1H, q), 4.81-4.70 (2H, m), 4.54-4.46 (2H, m), 4.32 (1H, q), 416-4.10 (1H, m), 4.10-3.85 (2H, m), 3.62-3.55 (1H, m), 2.58 (1H, d), 0.90-1.77 (4H, m).

EXAMPLE 6

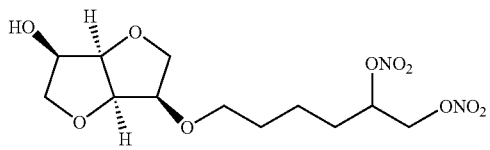

6-((3R,3aR,6R,6aR)-6-hydroxyhexahydrofuro[3,2-b]furan-3-yloxy)hexane-1,2-diyl dinitrate (corresponding to compound (23)

Step A: (3R,3aR,6R,6aR)-6-(hex-5-enyloxy)hexahydrofuro[3,2-b]furan-3-ol

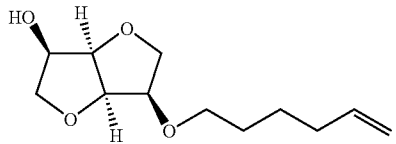

To a solution of 1,4:3,6-dianhydro-D-mannitol (4.00 g, 27.4 mmol) and Cs₂CO₃ (20.0 g, 60.2 mmol) in DMF (60 ml), 6-bromo-1-hexene (5.5 ml, 41.1 mmol), was added; the mixture was stirred at room temperature for 18 hrs. Then it was diluted with EtOAc and washed with a 5% solution of sodium dihydrogen phosphate (2×40 ml) and water (2×40 ml). The organic layer was dried over sodium sulfate, filtered, concentrated and purified by flash chromatography (Biotage SP1, EtOAc/n-hexane from 20 to 80%), affording the title compound.

Step B: 6-((3R,3aR,6R,6aR)-6-hydroxyhexahydrofuro[3,2-b]furan-3-yloxy)hexane-1,2-diyl dinitrate

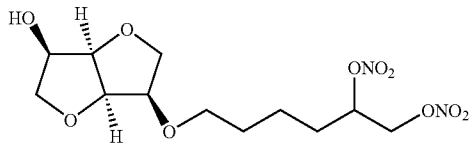

To an acetonitrile (32 ml) solution of (3R,3aR,6R,6aR)-6-(hex-5-enyloxy)hexahydrofuro[3,2-b]furan-3-ol (1.35 g, 5.91 mmol) at −20° C. was added silver nitrate (1.21 g, 7.12 mmol) and iodine (1.80 g, 7.10 mmol). The mixture was stirred at −20° C. for 10 minutes. Silver nitrate was added (2.51 g, 14.8 mmol) and the mixture was heated in a microwave apparatus (40 minutes, 120° C.). The silver salts were filtered off and the solution was concentrated. The residue was purified by flash chromatography (Biotage SP1, EtOAc/n-hexane from 30 to 100%), affording the title compound as colorless oil.

¹H-NMR (300 MHz, CDCl₃): δ 5.35-5.27 (1H, m), 4.76 (1H, dd), 4.58-.4.45 (3H, m), 4.35-4.25 (1H, m), 4.12-3.95 (3H, m), 3.75-3.65 (3H, m), 3.55-3.48 (1H, m), 2.86 (1H, d), 1.85-1.50 (6H, m).

EXAMPLE 7

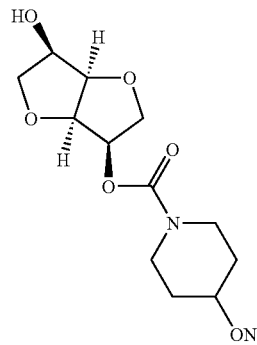

(3R,3aR,6R,6aR)-6-hydroxyhexahydrofuro[3,2-b]furan-3-yl 4-(nitrooxy)piperidine-1-carboxylate (corresponding to compound (27)

Step A: tert-butyl 4-(nitrooxy)piperidine-1-carboxylate

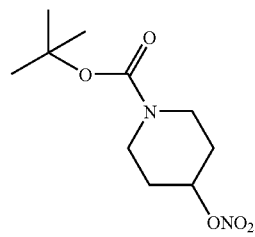

To a solution of tert-butyl 4-hydroxy-1-piperidinecarboxylate (2.00 g, 9.94 mmol), tetraethylammonium nitrate (3.82 g, 19.9 mmol) and 2,6-di-tert-butyl-4-methylpyridine (5.10 g, 24.9 mmol) in DCM (190 ml) cooled to −70° C. and under nitrogen, a solution of trifluoromethansulfonic anhydride (1.8 ml, 10.9 mmol) in DCM (62 ml) was added dropwise. The resulting mixture was stirred for 3 hrs at −65° C. Then the mixture was slowly warmed to room temperature, diluted with DCM and washed with 5% aqueous sodium dihydrogen phosphate. The organic layer was dried over sodium sulfate, filtered and concentrated, affording the title compound which was used in subsequent steps without further purification

Step B: Piperidin-4-yl nitrate hydrochloride

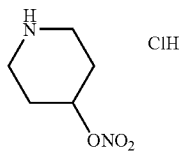

To a solution of tert-butyl 4-(nitrooxy)piperidine-1-carboxylate (2.10 g; 8.53 mmol) in DCM (15 ml) cooled to 0° C., HCl gas was bubbled for 2 hrs. The solvent was concentrated and the residue was treated with diethyl ether, affording the title compound which was used in subsequent steps without further purification.

Step C: (3R,3aR,6R,6aR)-6-hydroxyhexahydrofuro[3,2-b]furan-3-yl 4-nitrophenyl carbonate

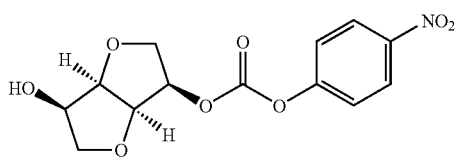

To a solution of 1,4:3,6-dianhydro-D-mannitol (3.00 g, 20.5 mmol) and triethylamine (3.15 ml, 22.6 mmol) in DCM (100 ml), 4-nitrophenyl chloroformate (4.55 g, 22.6 g) was added and the mixture was stirred at room temperature for 18 hrs. Then the mixture was washed with a 5% solution of sodium dihydrogen phosphate (2×50 ml). The organic layer was dried over sodium sulfate, filtered, concentrated and purified by flash chromatography (Biotage SP1, EtOAc/n-hexane from 20 to 80%), affording the title compound.

Step D: (3R,3aR,6R,6aR)-6-hydroxyhexahydrofuro[3,2-b]furan-3-yl 4-(nitrooxy)piperidine-1-carboxylate

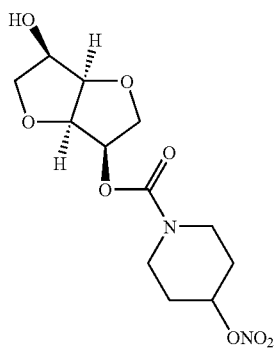

To a solution of piperidin-4-yl nitrate hydrochloride (0.620 g, 3.40 mmol), triethylamine (0.567 ml, 4.07 mmol) and 4-dimethylaminopyridine (0.083 g, 0.680 mmol) in DCM (23 ml), (3R,3aR,6R,6aR)-6-hydroxyhexahydrofuro[3,2-b]furan-3-yl 4-nitrophenyl carbonate (1.06 g, 3.40 mmol) was added; the mixture was stirred at room temperature for 18 hrs. Then the mixture was diluted with DCM and washed with a 5% solution of sodium dihydrogen phosphate (2×30 ml) and brine (1×30 ml). The organic layer was dried over sodium sulfate, filtered, concentrated and purified by flash chromatography (Biotage SP1, EtOAc/n-hexane from 30 to 100%), affording the title compound as a yellow oil.

$^1$H-NMR (300 MHz, CDCl$_3$):

EXAMPLE 8

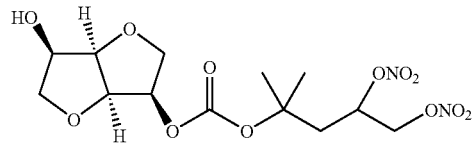

3,3-dimethyl-5,6-bis(nitrooxy)hexyl (3R,3aR,6R,6aR)-6-hydroxyhexahydrofuro[3,2-b]furan-3-yl carbonate (corresponding to compound (28)

Step A: 3,3-dimethyl-5,6-bis(nitrooxy)hexyl 4-nitrobenzoate

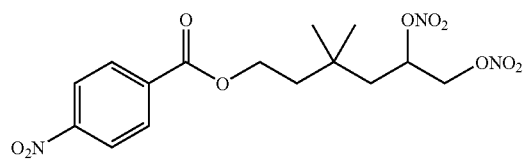

To an acetonitrile (60 ml) solution of 3,3-dimethylhex-5-enyl 4-nitrobenzoate (3.00 g, 10.8 mmol) at −20° C. was added silver nitrate (2.21 g, 13.0 mmol) and iodine (3.30 g, 13.0 mmol). The mixture was stirred at −20° C. for 10 minutes. Silver nitrate was added (4.6 g, 27.1 mmol) and the mixture was heated in a microwave apparatus (40 minutes, 120° C.). The silver salts were filtered off and the solution was concentrated. The residue was purified by flash chromatography (Biotage SP1, EtOAc/n-hexane from 20 to 80%), affording the title compound.

Step B: 6-hydroxy-4,4-dimethylhexane-1,2-diyl dinitrate

To a solution of 3,3-dimethyl-5,6-bis(nitrooxy)hexyl 4-nitrobenzoate (1.9 g, 4.73 mmol) in THF:EtOH 1:1 (12 ml) a aqueous solution of NaOH 3N (3.8 ml, 11.4 mmol) was added and the mixture was stirred at room temperature for 3 hrs. Then the mixture was diluted with a saturated solution of sodium bicarbonate and the product was extracted with EtOAc (3×30 ml). The organic layer was dried over sodium sulfate, filtered and concentrated under reduced pressure, affording the title compound which was used in the subsequent step without further purification.

Step C: 3,3-dimethyl-5,6-bis(nitrooxy)hexyl (3R, 3aR,6R,6aR)-6-hydroxyhexahydrofuro[3,2-b]furan-3-yl carbonate

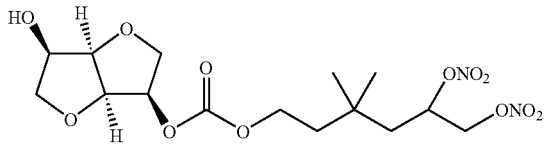

To a solution of (3R,3aR,6R,6aR)-6-hydroxyhexahydrofuro[3,2-b]furan-3-yl 4-nitrophenyl carbonate (0.962 g, 3.10 mmol) in DCM (40 ml), (prepared as described in EXAMPLE 7, Step C), 6-hydroxy-4,4-dimethylhexane-1,2-diyl dinitrate (0.780, 3.10 mmol) and 4-dimethylaminopyridine (0.379 g, 3.10 mmol) were added and the mixture was stirred at room temperature for 18 hrs. Then the mixture was diluted with DCM and washed with a 5% solution of sodium dihydrogen phosphate (2×30 ml) and brine (1×30 ml). The organic layer was dried over sodium sulfate, filtered and concentrated. The residue was purified by flash chromatography (Biotage SP1, EtOAc/n-hexane from 20 to 80%), affording the title compound.

$^1$H-NMR (300 MHz, CDCl$_3$): δ 5.52-5.43 (1H, m), 5.09 (1H, q), 4.80-.4.71 (2H, m), 4.52-4.40 (2H, m), 4.37-4.21 (3H, m), 4.15-3.90 (3H, m), 3.58 (1H, t), 2.53 (1H, d), 1.82-1.55 (4H, m), 1.03 (6H, m).

EXAMPLE 9

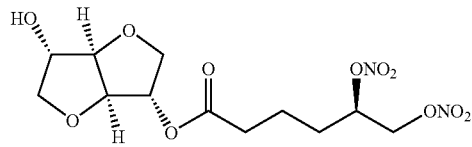

(3S,3aR,6S,6aR)-6-(2-chloropropanoyloxy)hexahydrofuro[3,2-b]furan-3-yl 5R,6-bis(nitrooxy)hexanoate (corresponding to compound (29) 5(R) isomer)

Step A: (3S,3aR,6S,6aR)-hexahydrofuro[3,2-b]furan-3,6-diyl dibenzoate

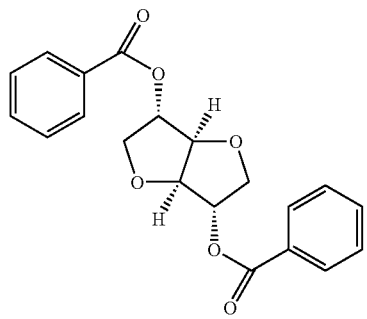

1,4:3,6-dianhydro-D-mannitol (3.00 g, 20.53 mmol) was dissolved in THF (40 ml). The solution was cooled (0° C.), then triphenylphosphine (11.85 g, 45.17 mmol), benzoic acid (5.52 g, 45.17 mmol) and diisopropyl azodicarboxylate (8.75 ml, 45.17 mmol) were added. The reaction was allowed to warm to room temperature and stirred for 12 hrs. Then the solvent was removed under reduced pressure and the residue was purified by flash chromatography (Biotage SP1, EtOAc/n-hexane from 10 to 30%), affording of the title compound as a white solid.

Step B: (3S,3aR,6S,6aR)-hexahydrofuro[3,2-b]furan-3,6-diol

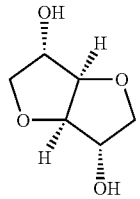

To (3S,3aR,6S,6aR)-hexahydrofuro[3,2-b]furan-3,6-diyl dibenzoate (6.30 g, 17.8 mmol), a mix of NaOH 10%: MeOH=1:1 (60 ml) was added. After stirring at room temperature for 24 hrs, the solvent was evaporated under reduced pressure. Water (30 ml) was added and extraction with EtOAc (30 ml) was carried out. The aqueous layer (pH adjusted to 6 with H$_3$PO$_4$ 5%) was evaporated under reduced pressure to leave a white residue. Tetrahydrofuran was added in a large amount, then the suspension was filtered and the filtrate was concentrated to give the title product as a white solid.

Step C: (3S,3aR,6S,6aR)-6-(tetrahydro-2H-pyran-2-yloxy)hexahydrofuro[3,2-b]furan-3-ol

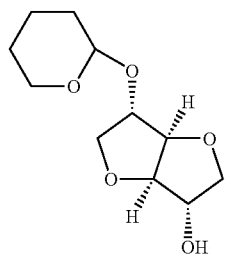

To a solution of (3S,3aR,6S,6aR)-hexahydrofuro[3,2-b]furan-3,6-diol (0.57 g, 3.90 mmol) and 3,4-dihydro-2H-pyran (0.41 g, 4.88 mmol) in DCM (15 ml), toluene-4-solfonic acid monohydrate (0.0074 g, 0.039 mmol) was added and the mixture was stirred at room temperature for 3 hrs. Then the reaction mixture was washed with a saturated solution of NaHCO$_3$ and brine. The organic extract was dried over sodium sulfate and the solvent, was evaporated under reduced pressure. The residue was purified by flash chromatography (Biotage SP1, EtOAc/n-hexane from 30 to 100%), affording the title product as a white solid.

Step D: (5R)-((3S,3aR,6S,6aR)-6-(tetrahydro-2H-pyran-2-yloxy)hexahydrofuro[3,2-b]furan-3-yl) 5,6-bis(nitrooxy)hexanoate

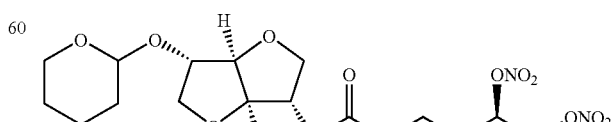

3S,3aR,6S,6aR)-6-(tetrahydro-2H-pyran-2-yloxy) hexahydrofuro[3,2-b]furan-3-ol (0.64 g, 2.80 mmol) and (5R)-5,6-bis-nitrooxy-hexanoic acid (1.18 g, 4.95 mmol) (obtained as described in EXAMPLE 5) were dissolved in DCM (30 ml), EDAC (0.81 g, 4.20 mmol) and 4-dimethylaminopyridine (0.068 g, 0.56 mmol) were added. After stirring at room temperature for 12 hrs, the reaction mixture was washed with water. The organic layer was dried over sodium sulfate, and evaporated under reduced pressure. The residue was purified by flash chromatography (Biotage SP1, EtOAc/n-hexane from 10 to 80%), affording the title product as an oil.

Step E: (3S,3aR,6S,6aR)-6-(2-chloropropanoyloxy) hexahydrofuro[3,2-b]furan-3-yl 5R,6-bis(nitrooxy) hexanoate

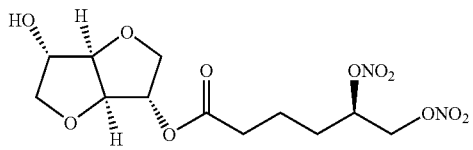

The title compound was obtained following the procedure described in EXAMPLE 4 Step G.

¹H-NMR (300 MHz, CDCl₃): δ 5.33 (1H, m), 5.20 (1H, m), 4.80-4.74 (1H, m), 7.67 (1H, d), 4.57-4.47 (2H, m), 4.39 (1H, s), 4.00-3.85 (4H, m), 2.48-2.39 (2H, m), 1.97 (1H, d), 1.90-1.73 (4H, m).

EXAMPLE 10

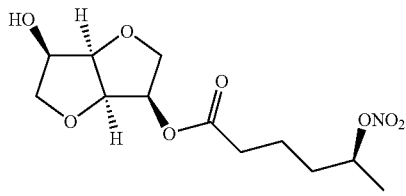

(S)-((3R,3aR,6R,6aR)-6-hydroxyhexahydrofuro[3,2-b]furan-3-yl) 5-(nitrooxy)hexanoate (corresponding to compound (20) 5(S) isomer)

Step A: (S)-tert-butyl 5-(nitrooxy)hexanoate

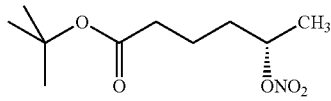

(S)-tert-butyl-5-hydroxyhexanoate (obtained as described in Oscar Pamies and Jan-E. Backvall, *J. Org. Chem.* 2002, 67, 1261-1265) (3.81 g, 20.2 mmol), 2,6-di-tert-butyl-4-methyl pyridine (6.64 g, 32.2 mmol), tetraethylammonium nitrate (7.76 g, 40.4 mmol) were dissolved in CH₂Cl₂ (75 mL). To the solution, cooled to −78° C., a solution of triflic anhydride (3.33 ml, 20.2 mmol) in CH₂Cl₂ (75 mL) was slowly added. The reaction was stirred at −78° C. for 30 minutes and then slowly warmed to room temperature and stirred for three hours. The mixture was then washed with NaH₂PO₄ and brine, dried over Na₂SO₄ and concentrated. The crude material was purified by flash chromatography (Biotage SP1, eluting with 2-20% EtOAc/Hexane) affording the title compound.

Step B: (S)-5-(nitrooxy)hexanoic acid

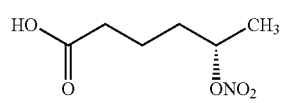

(S)-tert-butyl-5-(nitrooxy)hexanoate (590 mg, 2.53 mmol), was dissolved in CH₂Cl₂ (20 mL). HCl_gas was bubbled into the solution until the disappearance of the starting material. The solution was reduced to a small volume and diluted in CH₂Cl₂ few times to remove residual acidity, then used without further purification.

¹H NMR (300 MHz, CDCl₃): δ 9.01 (1H, bs); 5.09 (1H, m); 2.43 (2H, t); 1.70 (4H, m); 1.37 (3H, d)

Step C: (S)-((3R,3aR,6R,6aR)-6-hydroxyhexahydrofuro[3,2-b]furan-3-yl) 5-(nitrooxy)hexanoate

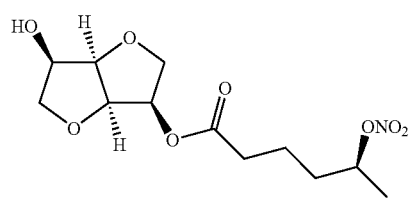

The title compound was prepared by following the procedure for the synthesis of EXAMPLE 4, except that in Step F the reagent (S)-5,6-di(nitrooxy)hexanoic acid was replaced by (S)-5-(nitrooxy)hexanoic acid.

¹H NMR (300 MHz, CDCl₃): δ 5.24-4.99 (1H, m); 5.09 (2H, m); 4.71 (1H, t); 4.50 (1H, t); 4.30 (1H, m); 4.12 (1H, m); 3.97 (1H, m); 3.86 (1H, m); 3.57 (1H, m), 2.61 (1H, d); 2.43 (2H, m); 1.91-1.51 (4H, m); 1.37 (3H, d).

EXAMPLE 11

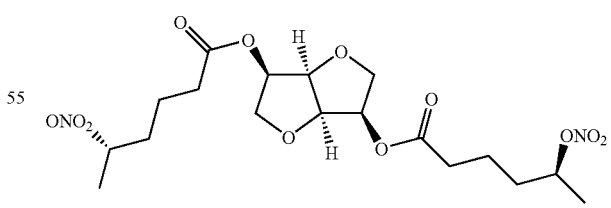

(5S,5'S)-((3R,3aR,6R,6aR)-hexahydrofuro[3,2-b]furan-3,6-diyl) bis(5-(nitrooxy)hexanoate) (corresponding to compound (30) 5(S) isomer)

The title compound was prepared by following the procedure for the synthesis of EXAMPLE 1, except that in Step A the reagent 5-hexenoic acid was replaced by 2 equivalents of (S)-5-(nitrooxy)hexanoic acid.

$^1$H NMR (300 MHz, CDCl$_3$): δ 5.10 (4H, m); 4.71 (2H, m); 4.04 (2H, dd); 3.80 (2H, dd); 2.43 (4H, m); 1.87-1.62 (8H, m); 1.39 (6H, d).

EXAMPLE 12

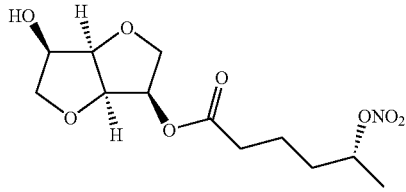

(R)-((3R,3aR,6R,6aR)-6-hydroxyhexahydrofuro[3,2-b]furan-3-yl) 5-(nitrooxy)hexanoate (corresponding to compound (20) 5(R) isomer)

The title compound was prepared by following the procedure for the synthesis of EXAMPLE 10, except that in Step C the reagent (S)-5-(nitrooxy)hexanoic acid was replaced by (R)-5-(nitrooxy)hexanoic acid obtained as described in Oscar Pamies and Jan-E. Backvall, *J. Org. Chem.* 2002, 67, 1261-1265) and EXAMPLE 10.

$^1$H NMR (300 MHz, CDCl$_3$): δ 5.24-4.99 (1H, m); 5.09 (2H, m); 4.71 (1H, t); 4.50 (1H, t); 4.30 (1H, m); 4.12 (1H, m); 3.97 (1H, m); 3.86 (1H, m); 3.57 (1H, m), 2.61 (1H, d); 2.43 (2H, m); 1.91-1.51 (4H, m); 1.37 (3H, d).

EXAMPLE 13

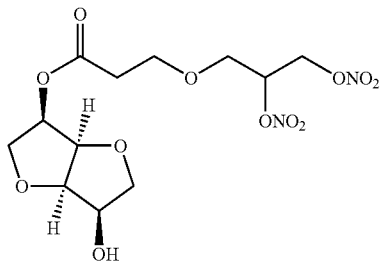

(3R,3aR,6R,6aR)-6-hydroxyhexahydrofuro[3,2-b]furan-3-yl 3-(2,3-bis(nitrooxy)propoxy)propanoate (corresponding to compound (3))

Step A: 3-(2,3-bis(nitrooxy)propoxy)propanoic acid

The title compound was prepared by following the procedure described in EXAMPLE 8 Step A,B except that the reagent 3,3-dimethylhex-5-enyl 4-nitrobenzoate was replaced by 4-nitrophenyl 3-(allyloxy)propanoate and the reagent 3,3-dimethyl-5,6-bis(nitrooxy)hexyl 4-nitrobenzoate was replaced by 4-nitrophenyl 3-(2,3-bis(nitrooxy)propoxy) propanoate.

Step B: (3R,3aR,6R,6aR)-6-hydroxyhexahydrofuro[3,2-b]furan-3-yl 3-(2,3-bis(nitrooxy)propoxy)propanoate The title compound was prepared by following the procedure for the synthesis of EXAMPLE 4, except that in Step F the reagent (S)-5,6-di(nitrooxy)hexanoic acid was replaced by 3-(2,3-bis(nitrooxy)propoxy)propanoic acid obtained as described in Oscar Pamies and Jan-E. Backvall, *J. Org. Chem.* 2002, 67, 1261-1265) and EXAMPLE 10.

$^1$H NMR (300 MHz, CDCl$_3$): δ 5.41 (1H, m); 5.20 (1H, q); 4.86-4.76 (1H, m); 4.75-4.60 (2H, m); 4.51 (1H, t); 4.32 (1H, m); 4.14 (1H, m); 3.98 (1H, m); 3.93-3.71 (5H, m), 3.59 (1H, m); 2.67 (2H, t); 2.59 (1H, d).

EXAMPLE 14

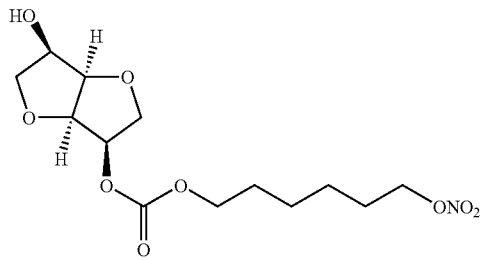

(3R,3aR,6R,6aR)-6-hydroxyhexahydrofuro[3,2-b]furan-3-yl 6-(nitrooxy)hexyl carbonate (corresponding to compound (31)

Step A: (3R,3aR,6R,6aR)-6-hydroxyhexahydrofuro[3,2-b]furan-3-yl 6-chlorohexyl carbonate

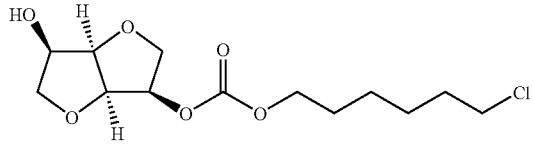

To a solution of (3R,3aR,6R,6aR)-6-hydroxyhexahydrofuro[3,2-b]furan-3-yl 4-nitrophenyl carbonate (1.13 g, 3.63 mmol) in DCM (15 ml), (prepared as described in EXAMPLE 7, Step C), 6-chlorohexanol (596 mg, 4.36 mmol) and 4-dimethylaminopyridine (89 mg, 0.73 mmol) were added and the mixture was stirred at room temperature for 18 hrs. Then the mixture was diluted with DCM and washed with a 5% solution of sodium dihydrogen phosphate (20 ml). The organic layer was dried over sodium sulfate, filtered and concentrated in vacuo. The residue was purified by flash chromatography (Biotage SP1, EtOAc/n-hexane from 12 to 80%), affording the title compound as colorless oil.

$^1$H NMR (300 MHz, DMSO) δ 5.02-4.85 (2H, m), 4.62 (1H, t), 4.29 (1H, t), 4.17 (3H, t), 3.93-3.82 (1H, m), 3.82-3.71 (2H, m), 3.63 (2H, t), 1.81-1.66 (3H, m), 1.66-1.54 (2H, m), 1.48-1.27 (4H, m).

Step B: (3R,3aR,6R,6aR)-6-hydroxyhexahydrofuro[3,2-b]furan-3-yl 6-(nitrooxy)hexyl carbonate

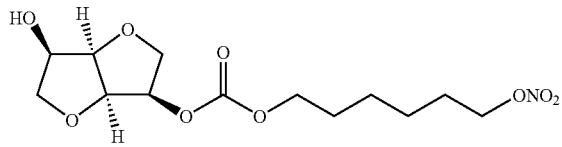

To an acetonitrile (6 ml) solution of (3R,3aR,6R,6aR)-6-hydroxyhexahydrofuro[3,2-b]furan-3-yl 6-chlorohexyl carbonate (277 mg, 0.90 mmol) was added silver nitrate (457 mg, 2.69 mmol) and the mixture was heated in a microwave apparatus (40 minutes, 125° C.). The silver salts were filtered off, the solution was concentrated in vacuo and DCM was added (50 ml). The mixture was washed with water (2×30 ml) dried over sodium sulfate, filtered and concentrated under reduce pressure. The residue was purified by flash chromatography (Biotage SP1, EtOAc/n-hexane from 10 to 100%), affording the title compound as colorless oil.

$^1$H NMR (300 MHz, CDCl$_3$) δ 5.09 (1H, m) 4.76 (1H, t), 4.54-4.42 (3H, m), 4.38-4.25 (1H, m), 4.24-4.14 (2H, m), 4.14-4.07 (1H, m), 4.05-3.91 (2H, m), 3.64-3.52 (1H, m), 2.56 (1H, d), 1.84-1.65 (4H, m), 1.53-1.38 (4H, m).

Assay on Vascular Tone

The ability of the compounds of the invention to induce vasorelaxation in comparison to precursor compounds, was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, NaHCO$_3$ 14.9, KH$_2$PO$_4$ 1.2, MgSO$_4$ 1.2, HEPES 10, CaCl$_2$, ascorbic acid 170 and glucose 1.1 (95% O$_2$/5% CO$_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 μM) and, when the contraction was stable, acetylcholine (ACh, 10 μM) was added. A relaxant response to ACh indicated the presence of a functional endothelium. Vessels that were unable to contract NA or showed no relaxation to Ach were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 μM) for 20 min.

Responses to relaxing agents are expressed as a percentage of residual contraction and plotted against concentration of test compound. EC$_{50}$ values (where EC$_{50}$ is the concentration producing 50% of the maximum relaxation to the test compound) were interpolated from these plots. During the experimental period, the plateau obtained with NA was stable without significant spontaneous loss of contraction in the aortic rings. Under these experimental conditions, the precursor compound (isomannide) does not produce relaxation at any of the concentration tested, the curve being not different from that built up in the presence of vehicle alone.

As shown in Table 1, the compounds of the present invention were able to induce relaxation in a concentration-dependent manner. Furthermore, in experiments performed in the presence of ODQ (10 μM), the vasorelaxant responses to tested compounds were inhibited.

TABLE 1

| Compound | EC$_{50}$ (μM) ± sem |
|---|---|
| Isomannide | no effect |
| Example 1 | 0.11 ± 0.03 |
| Example 2 | 3.10 ± 0.9 |
| Example 3 | 2.5 ± 0.6 |
| Example 4 | 0.11 ± 0.02 |
| Example 6 | 0.91 ± 0.33 |
| Example 7 | 4.4 ± 1.9 |
| Example 8 | 0.06 ± 0.01 |
| Example 9 | 0.11 ± 0.02 |
| Example 13 | 0.10 ± 0.03 | cGMP Accumulation Assay

The ability of the compounds of the invention to increase intracellular cGMP in comparison to vehicle was tested in vitro in Human Embryonic Kidney (HEK293) cell preparations. The method followed was as that reported in literature with minor modifications (Ongini et al., PNAS 2004; 101 (22):8497-502. Ronchetti et al., Eur J. Pharmacol. 2006; 532 (1-2):162-9).

Briefly, HEK293 cells were washed once with Hank's Balance Salt Solution (HESS) supplemented with HEPES (10 mM), MgCl$_2$ (5 mM) and 0.05% ascorbic acid. Then they were pre-incubated for 20 min with a nitric oxide synthase inhibitor, N-nitro-L-arginine methyl ester (L-NAME) (300 μM) so to lower endogenous NO production. The cells were then exposed for 30 min to either vehicle (DMSO 1%) or increasing concentrations of test compounds (up to 100 μM) in presence of the phosphodiesterase inhibitor, 3-isobutyl-1-methylxanthine (IBMX, 100 μM) and the NO-independent activator/modulator of soluble guanylyl-cyclase, BAY 41-2272 (1 μM). The reaction was ended by the removal of the incubating buffer and the addition of 50 μl/well of 100% ice-cold ethanol. The plate was then dried under hot air steam and the cell residues dissolved, extracted and analysed using commercially available cyclic GMP enzyme immunoassay kit (Cayman Chemical, Ann Arbor, Mich., U.S.A.). Data obtained with the compounds of the present invention, expressed as % of vehicle at their respective maximal concentration (100 μM), are reported in Table 2.

TABLE 2

| Compound | % of vehicle (mean ± sem at 100 μM) |
|---|---|
| Vehicle (DMSO 1%) | 100 ± 18.0 |
| Example 1 | 1029.6 ± 80.2 |
| Example 2 | 1082.67 ± 163.4 |
| Example 3 | 677.83 ± 79.6 |
| Example 4 | 986.3 ± 90.0 |
| Example 5 | 668 ± 64.7 |

TABLE 2-continued

| Compound | % of vehicle (mean ± sem at 100 μM) |
|---|---|
| Example 6 | 1620 ± 205.0 |
| Example 8 | 564 ± 59.0 |
| Example 13 | 683 ± 86.3 |

Assay for Antihypertensive Activity (In Vivo)

The ability of the compounds of the invention to decrease blood pressure was evaluated in conscious spontaneously hypertensive rats (SHRs). SHRs (250-300 g) received a single oral dose of tested compounds. Systolic blood pressure (SBP) and heart rate were monitored by telemetry for 24 hours after dosing. SBP was evaluated before (baseline) and at different time points (i.e. 2-6, 12, 21-24, 25-48 hours) following treatment by oral administration of the compounds. The data were processed both as the absolute value or as a delta between the absolute value and its own baseline.

The Dataquest IV telemetry system (Data Sciences International) was used for measurement of systolic pressure, diastolic pressure, mean arterial pressure, heart rate, and motor activity. The monitoring system consists of a transmitter (radio frequency transducer model TA11PA), receiver panel, consolidation matrix, and personal computer with accompanying software. Before the device was implanted, calibrations were verified to be accurate within ±3 mmHg. Rats were anesthetized with ketamine/xylazine/acepromazine, and the flexible catheter of the transmitter was surgically secured in the abdominal aorta just below the renal arteries. The transmitter was sutured subcutaneously. Rats were housed in individual cages after the operation. Each cage was placed over the receiver panel that was connected to the personal computer for data acquisition. The rats were unrestrained and free to move within their cages. Hemodynamic data were sampled every 2 minutes for 10 seconds.

Compared to precursor compound (isomannide), the compound of Example 1 provided BP lowering with extended peak effect and duration of action (Table 3).

TABLE 3

| | Δ SBP in SHR (mmHg) | | | |
|---|---|---|---|---|
| Compound | 2-6 hrs | 12 hrs | 21-24 hrs | 25-48 hrs |
| Isomannide (2.4 mpk) | −3 | −9 | −6 | −6 |
| Example 1 (4.4 mpk) | −13 | −16 | −20 | −16 |

The invention claimed is:

1. A compound of the formula (I) and pharmaceutically acceptable salts or stereoisomers thereof:

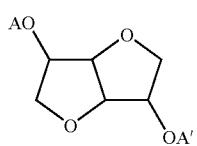

(I)

wherein A and A' are independently selected from the group consisting of H and —(X)$_s$—Y with the proviso that at least one of A or A' is not H and at least one of A or A' is H;

wherein s is 0 or 1;

X is selected from the group consisting of:

—CO—, —COO—, —CONH— and —SO$_2$— or

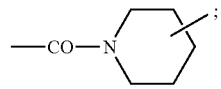

Y is selected from the group consisting of:

1) Z—CH$_2$—ONO$_2$, wherein Z is a straight or branched $C_1$-$C_{10}$ alkylene;

2) (CH$_2$)$_n$R$^1$, 3) (CH$_2$)$_n$—O—CH$_2$—R$^1$, wherein

R$^1$ is —CH(ONO$_2$)R$^2$;

R$^2$ is —CH$_3$ or $C_{1-4}$ alkyl;

n is an integer from 1 to 6;

4) Y$^1$—R$^3$, wherein

R$^3$ is —CH(ONO$_2$)CH(ONO$_2$)R$^4$;

R$^4$ is selected from —CH$_3$, —CH$_2$CH$_3$ and —CH(CH$_3$)$_2$;

Y$^1$ is —(CH$_2$)$_{1-4}$—(X$^1$)$_{0-1}$—(CH$_2$)$_{0-4}$, wherein X$^1$ is —O— or —CR$^5$R$^6$—; and R$^5$ and R$^6$ are independently selected from the group consisting of hydrogen and $C_1$-$C_4$ alkyl; and

5) Y$^1$—CH(ONO$_2$)CH$_2$(ONO$_2$)

wherein Y$^1$ is as above defined, with the proviso that when s is 0, then Y$^1$ is not —CH$_2$—.

2. A compound of formula (I) according to claim 1 selected from the group consisting of:

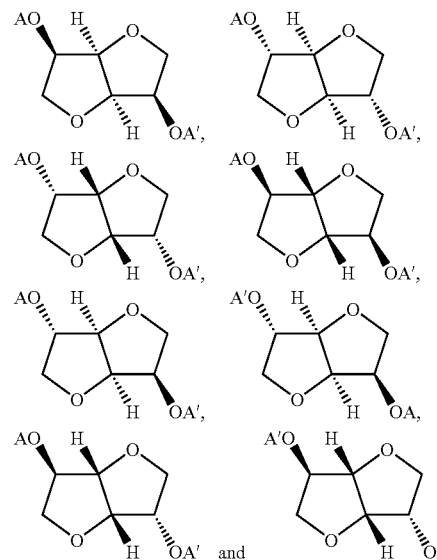

wherein A and A' are as defined in claim 1.

3. A compound of formula (I) according to claim 1 selected from the group consisting of:

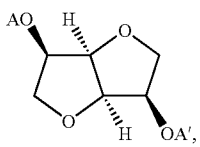 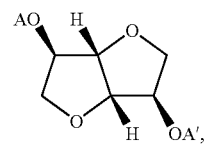

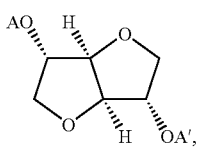 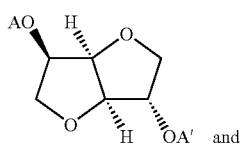 and

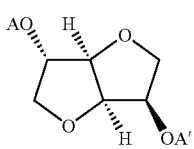

wherein A and A' are as defined in claim 1.

4. A compound of formula (I) according to claim 1, wherein the compound is selected from the group consisting of:

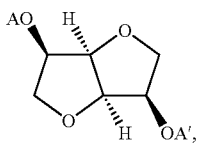 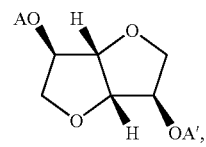

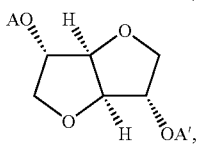 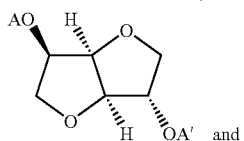 and

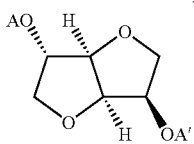

wherein A is H and A' is —CO—Y or —COO—Y.

5. A compound of formula (I) according to claim 1, wherein the compound is selected from the group consisting of:

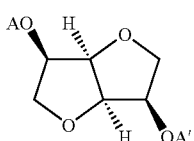 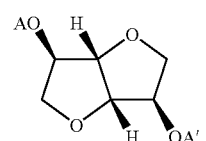

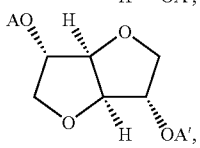 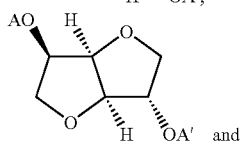 and

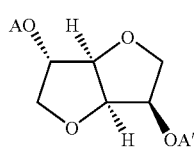

wherein A is H, A' —(X)$_s$—Y wherein s is 0.

6. A compound of formula (I) according to claim 1 wherein the compound is selected from the group consisting of:

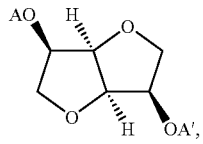 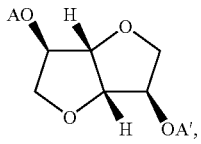

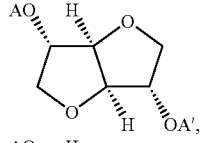 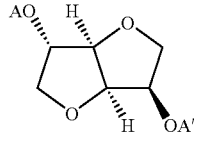 and wherein A is H and A' is

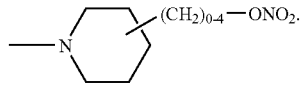

7. A compound of formula (I) according to claim 1, Y is selected from the group consisting of:

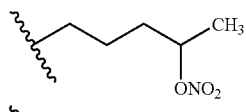

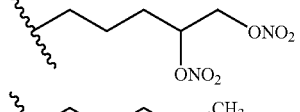

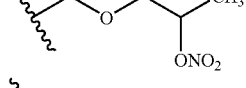

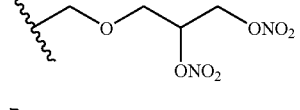

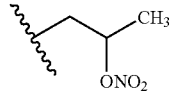

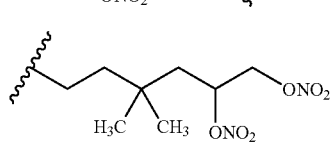

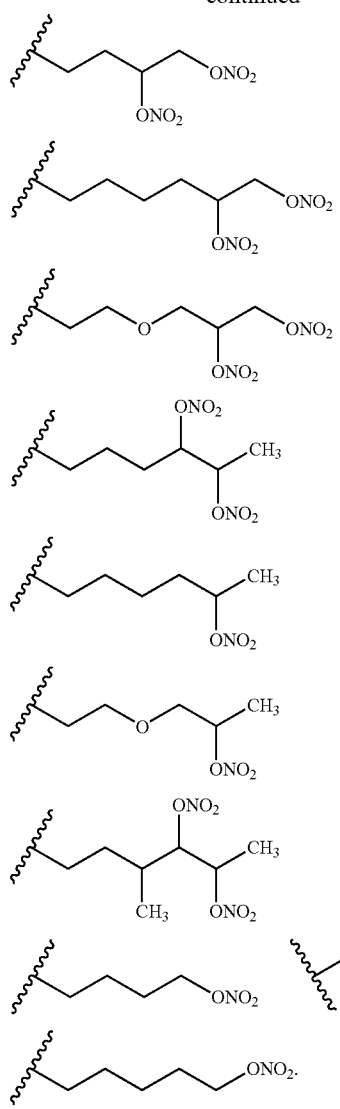
8. A compound of formula (I) according to claim 1 selected from the group consisting of:
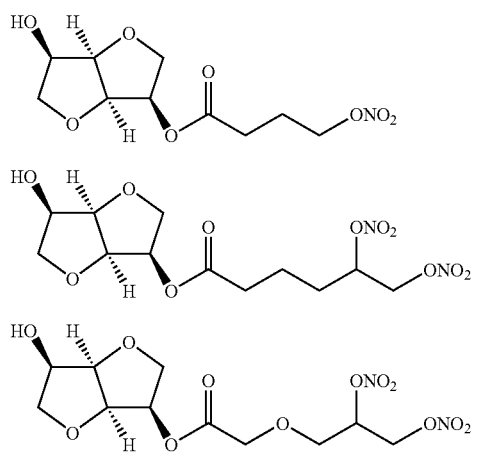
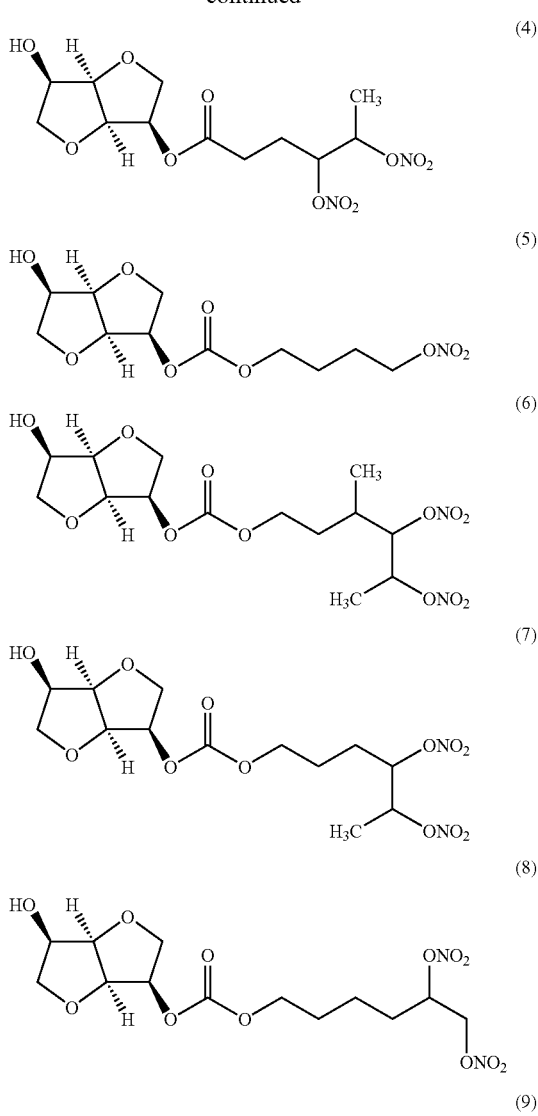
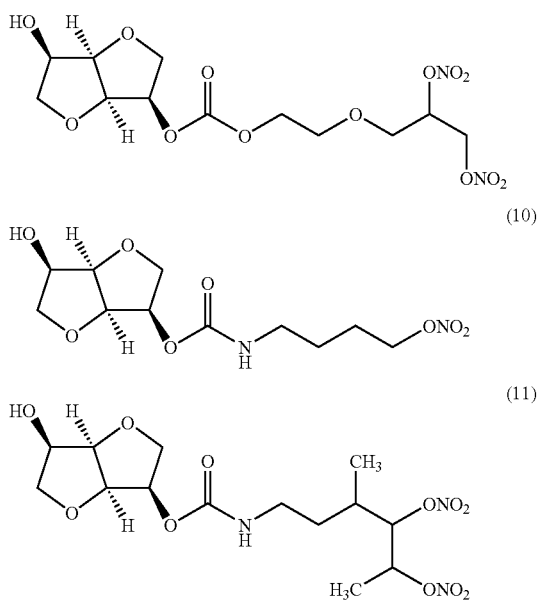

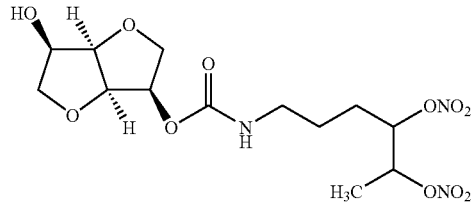 (12)
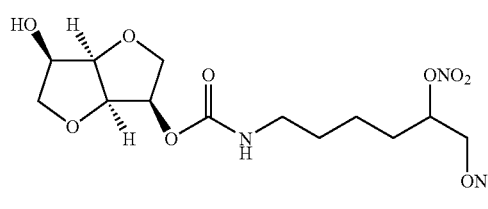 (13)
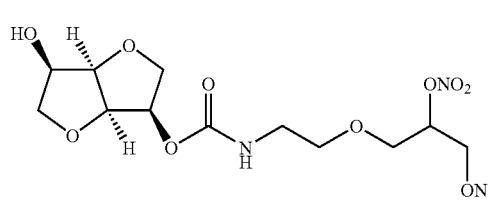 (14)
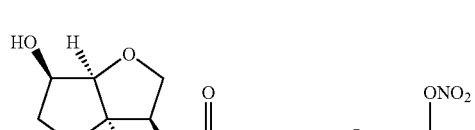 (15)
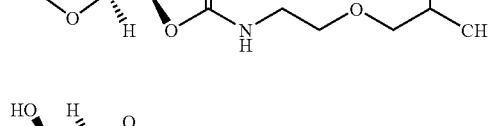 (16)
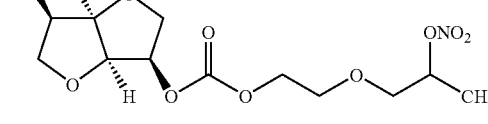 (17)
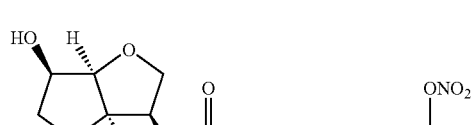 (18)
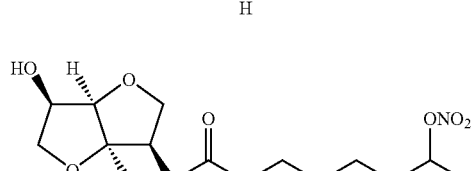 (19)
(20)
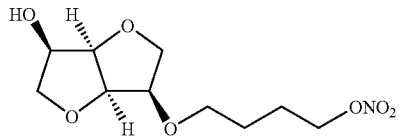 (21)
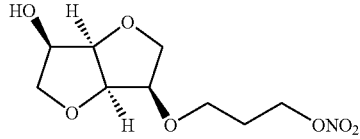 (22)
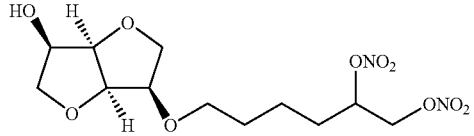 (23)
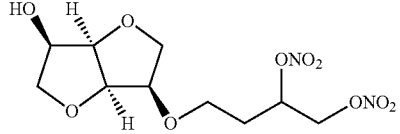 (24)
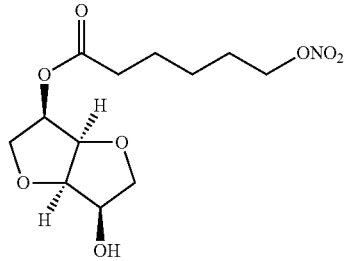 (25)
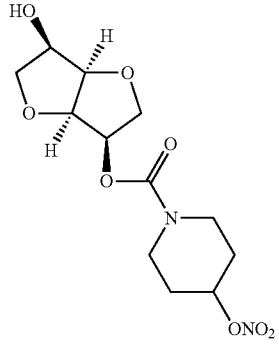 (27)
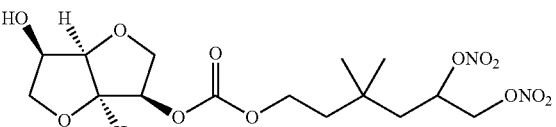 (28)
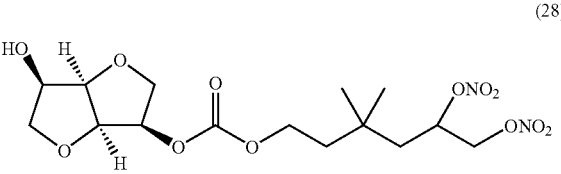 (28)

-continued

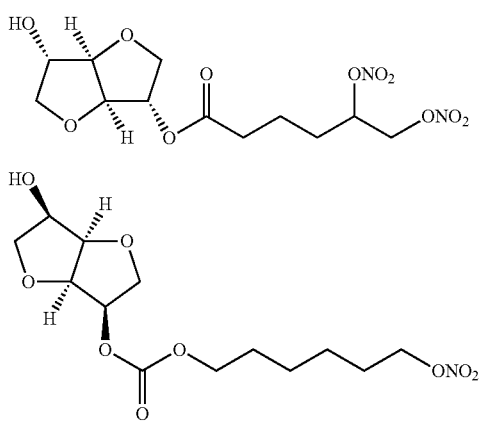

(29)

(31)

or steroisomers thereof.

9. A medicament comprising a compound of formula (I) or pharmaceutically acceptable salts or stereoisomers thereof according to claim 1.

10. A combination comprising a compound of formula (I) or pharmaceutically acceptable salts or stereoisomers thereof according to claim 1 and at least one therapeutic agent selected from:

non steroidal anti-inflammatory drugs, anti-thrombotic drugs, steroidal anti-inflammatory drugs, ACE inhibitors, Angiotensin II receptor antagonist, β-adrenergic receptor blockers, β-adrenergic receptor agonists, statins, prostaglandins.

11. Pharmaceutical formulation comprising a compound of formula (I) or pharmaceutically acceptable salts or stereoisomers thereof according to claim 1 and a pharmaceutical acceptable excipient.

12. The compound of claim 1, wherein Z is a straight or branched $C_1$-$C_6$ alkylene.

* * * * *